(12) United States Patent
Choi et al.

(10) Patent No.: US 11,204,668 B2
(45) Date of Patent: Dec. 21, 2021

(54) ELECTRONIC DEVICE AND METHOD FOR ACQUIRING BIOMETRIC INFORMATION USING LIGHT OF DISPLAY

(71) Applicant: Samsung Electronics Co., Ltd., Gyeonggi-do (KR)

(72) Inventors: Woojhon Choi, Gyeonggi-do (KR); Duseon Oh, Gyeonggi-do (KR); Dasom Kim, Gyeonggi-do (KR); Jinho Kim, Gyeonggi-do (KR); Jiwoon Jung, Gyeonggi-do (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 15/930,545

(22) Filed: May 13, 2020

(65) Prior Publication Data
US 2020/0363902 A1 Nov. 19, 2020

(30) Foreign Application Priority Data
May 14, 2019 (KR) .................. KR10-2019-0056177

(51) Int. Cl.
*G06K 9/00* (2006.01)
*G06F 3/041* (2006.01)
*G06F 3/042* (2006.01)

(52) U.S. Cl.
CPC .......... *G06F 3/0421* (2013.01); *G06F 3/0414* (2013.01); *G06F 3/0416* (2013.01); *G06F 3/0425* (2013.01); *G06K 9/0004* (2013.01)

(58) Field of Classification Search
CPC .... G06F 3/0416; G06F 3/0421; G06F 3/0425; G06F 3/0414; G06K 9/0004;
(Continued)

(56) References Cited

U.S. PATENT DOCUMENTS

| | | |
|---|---|---|
| 9,444,998 B2 | 9/2016 | Kim et al. |
| 2016/0180141 A1 | 6/2016 | Sarve et al. |

(Continued)

FOREIGN PATENT DOCUMENTS

| | | |
|---|---|---|
| KR | 10-2015-0098158 A | 8/2015 |
| WO | 2019/062471 A1 | 4/2019 |

OTHER PUBLICATIONS

International Search Report dated Sep. 9, 2020.

*Primary Examiner* — Jonathan A Boyd
(74) *Attorney, Agent, or Firm* — Cha & Reiter, LLC

(57) ABSTRACT

An electronic device according to an embodiment may include a housing, a display exposed through at least part of a first surface of the housing, an image sensor, a processor operatively connected with the display and the image sensor, and a memory operatively connected with the processor, wherein the memory may store instructions that, when executed, cause the processor to detect a touch of a finger of a user on the image sensor, while displaying a user interface using the display, in response to detecting the touch, while the touch of the finger is maintained on the image sensor, change the user interface in an area of the display within a preset distance from the image sensor, and acquire biometric information of the user based on reflection light of light emitted from the display, where the reflection light is acquired using the image sensor.

20 Claims, 12 Drawing Sheets

(58) Field of Classification Search
CPC ......... H04M 1/72454; H04M 1/72469; H04M 2250/12; H04M 2201/34; H04M 2201/36; H04M 2201/38
See application file for complete search history.

(56) References Cited

U.S. PATENT DOCUMENTS

2017/0337542 A1\* 11/2017 Kim .................... G06Q 20/367
2018/0074627 A1\* 3/2018 Kong .................... G06F 21/32
2018/0129798 A1\* 5/2018 He ......................... G06F 3/042
2018/0189468 A1\* 7/2018 Shim ................ G06K 9/00006
2018/0333088 A1 11/2018 Holz et al.
2019/0114458 A1 4/2019 Cho et al.
2019/0243417 A1\* 8/2019 Cheng ................ H04M 1/0266

\* cited by examiner

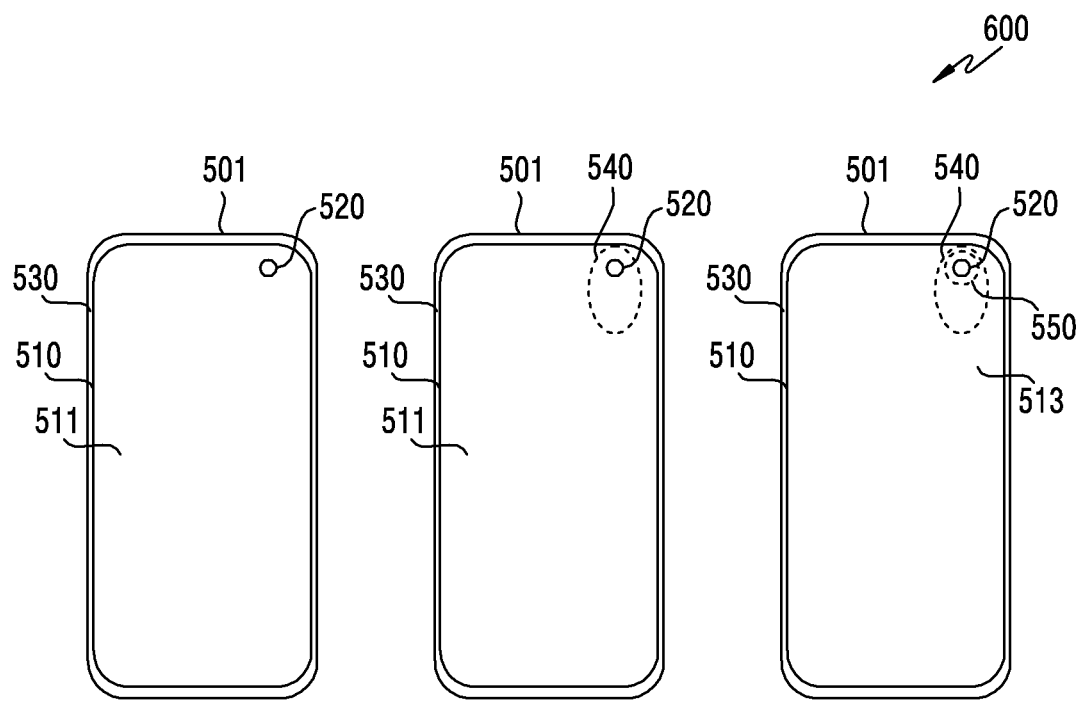
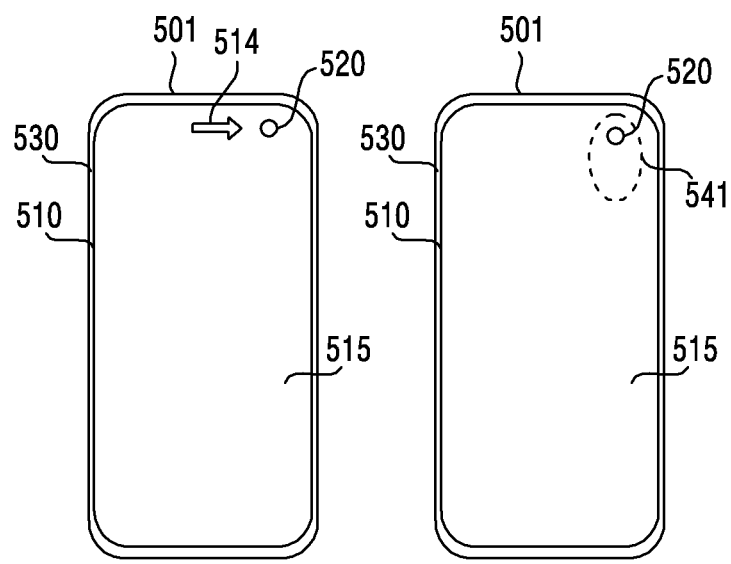
FIG.5A  FIG.5B  FIG.5C
FIG.5D  FIG.5E

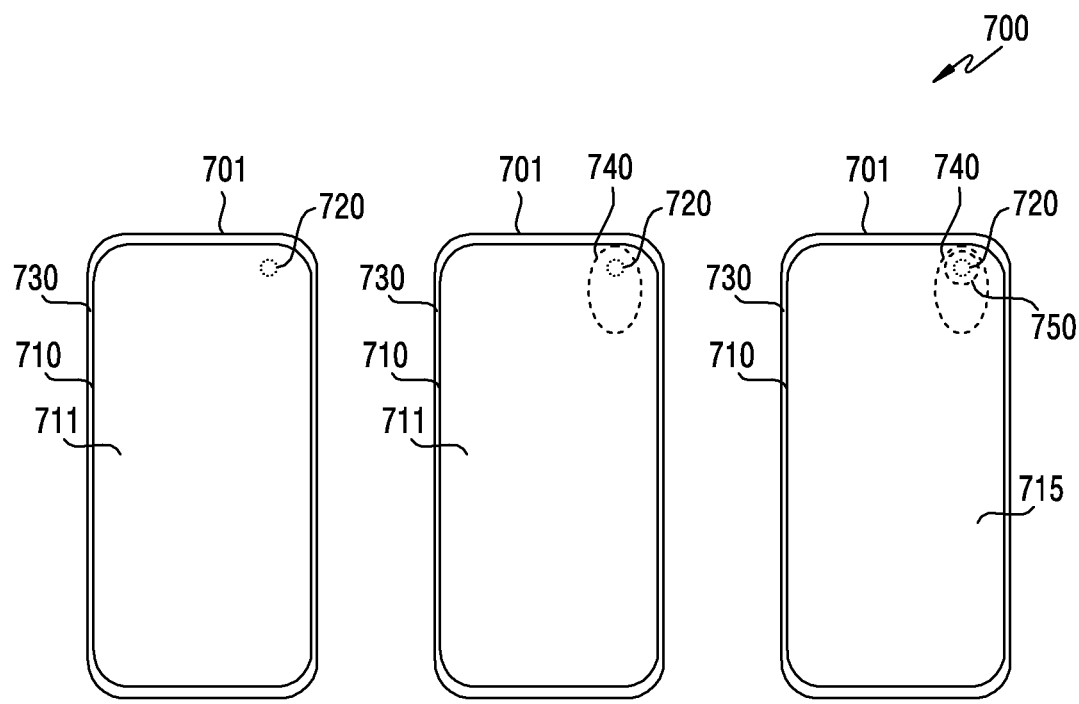
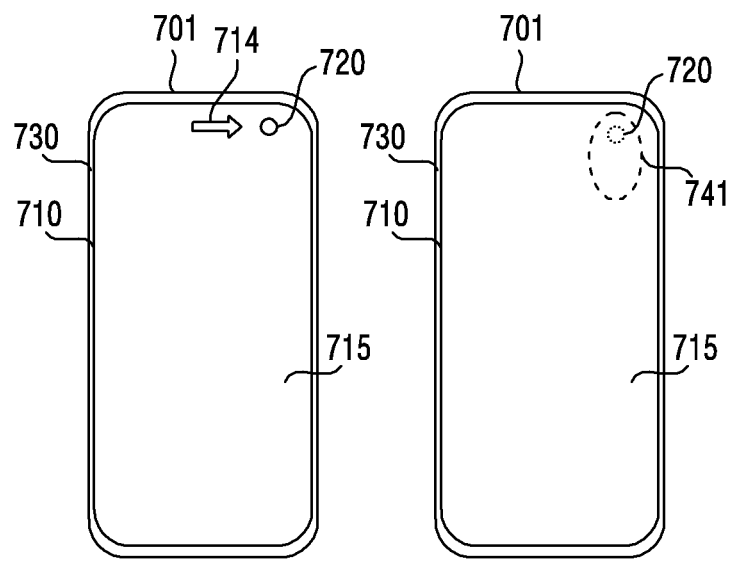
FIG.7A  FIG.7B  FIG.7C
FIG.7D  FIG.7E

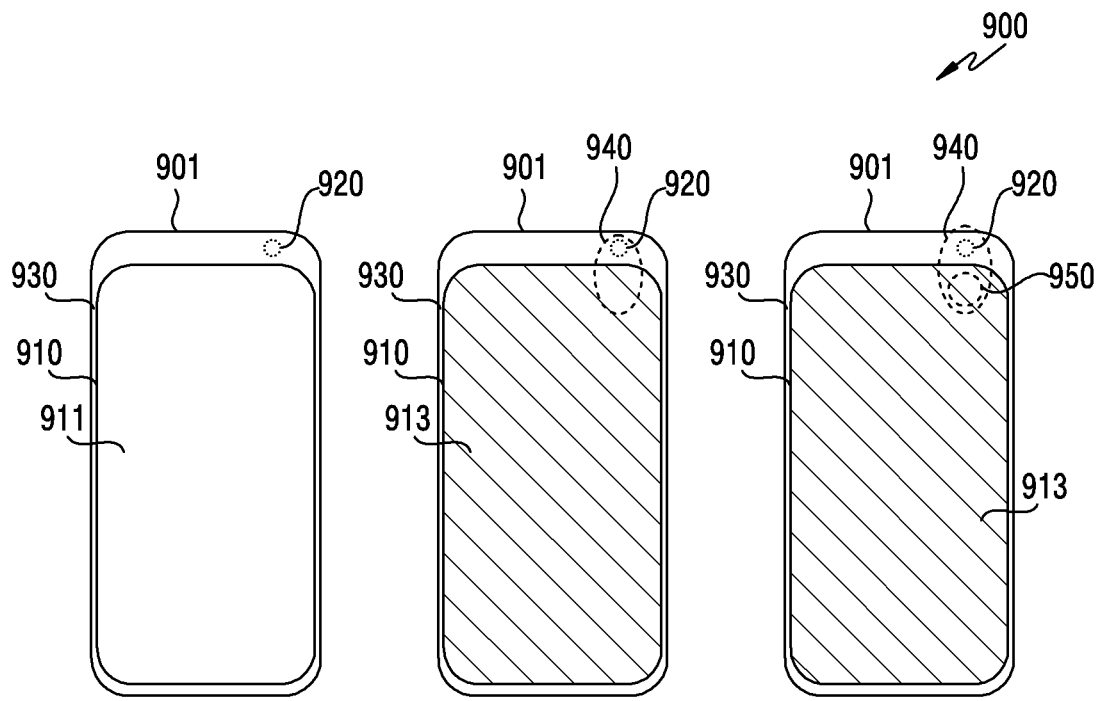
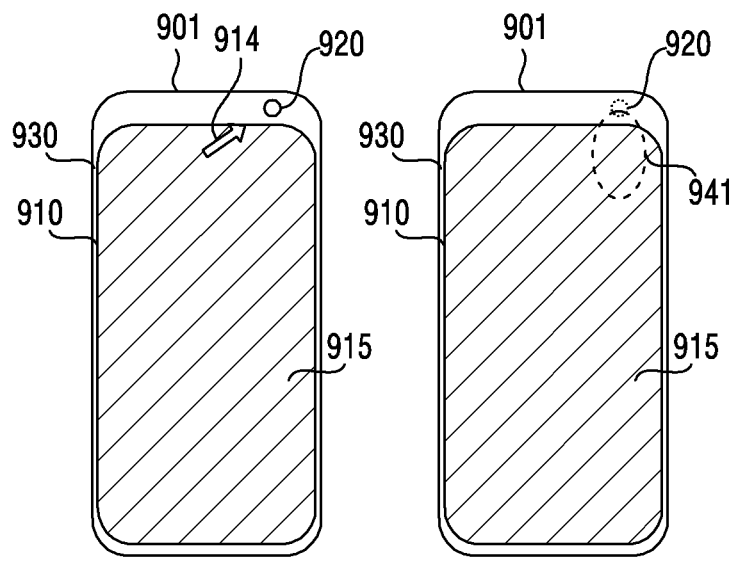

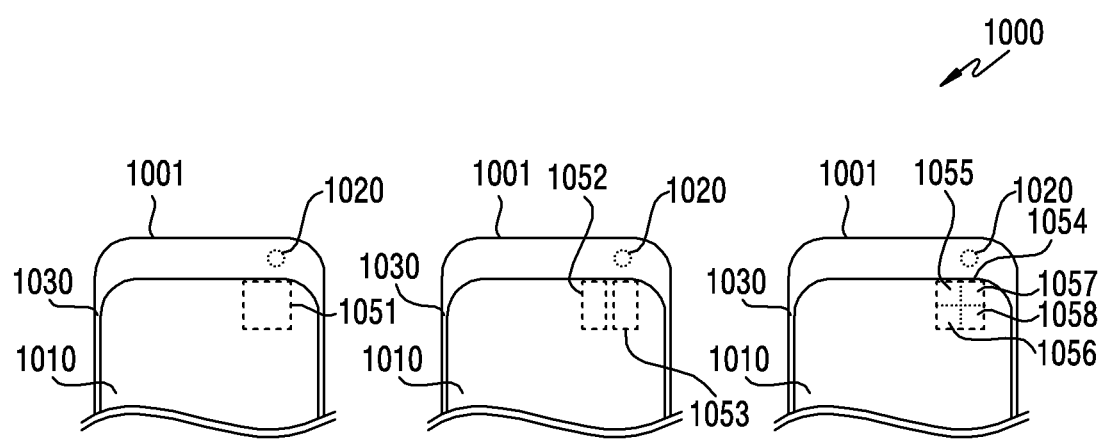

ELECTRONIC DEVICE AND METHOD FOR ACQUIRING BIOMETRIC INFORMATION USING LIGHT OF DISPLAY

CROSS-REFERENCE TO RELATED APPLICATION(S)

This application is based on and claims priority under 35 U.S.C. § 119 to Korean Patent Application No. 10-2019-0056177, filed on May 14, 2019, in the Korean Intellectual Property Office, the disclosure of which is incorporated by reference herein in its entirety.

TECHNICAL FIELD

The present disclosure generally relates to an electronic device and a method for acquiring biometric information using the light of a display.

BACKGROUND

An electronic device may acquire user's biometric information using a light sensor. To acquire the user's biometric information, the electronic device requires a light emitting device and the light sensor.

SUMMARY

Conventionally, an electronic device may require dedicated light emitting device and light sensor, in order to provide the user with various functions associated with biometric information. In addition, since the light emitting device and the light sensor are exposed on a surface of a housing of the electronic device, design of the electronic device may be limited, and the cost for purchasing and installing the light emitting device and the light sensor increases.

Hence, research into acquisition of biometric information without needing dedicated light emitting device and light sensor has been conducted.

An electronic device according to an embodiment may include a housing, a display exposed through at least part of a first surface of the housing, an image sensor exposed through at least part of the first surface of the housing, a processor operatively connected with the display and the image sensor, and a memory operatively connected with the processor, and the memory may store instructions that, when executed, cause the processor to detect a touch of a finger of a user on the image sensor, while displaying a user interface using the display, in response to detecting the touch, while the touch of the finger is maintained on the image sensor, change the user interface in an area of the display within a preset distance from the image sensor, and acquire biometric information of the user based on reflection light of light emitted from the display, where the reflection light is acquired using the image sensor.

An operating method of an electronic device that includes a housing according to an embodiment may include, while displaying a user interface using a display exposed through at least part of a first surface of the housing, detecting a touch of a finger of a user on an image sensor exposed through at least part of the first surface of the housing, in response to detecting the touch, while the touch of the finger is maintained on the image sensor, changing the user interface in an area of the display within a preset distance from the image sensor, and acquiring biometric information of the user based on reflection light of light emitted from the display, where the reflection light is acquired using the image sensor.

An electronic device according to an embodiment may include a housing, a display exposed through at least part of a first surface of the housing, an image sensor disposed in a display area of the display, when viewing the first surface of the housing, a processor operatively connected with the display and the image sensor, and a memory operatively connected with the processor, and the memory may store instructions that, when executed, cause the processor to display an indicator indicating a preset touch request area, on a user interface displayed on the display, detect a touch of a finger of a user, in at least part of the touch request area after the indicator is displayed in the user interface, in response to detecting the touch, control the display to emit light of a preset intensity in a preset second area which surrounds the image sensor, when viewed in a front view of the housing, and acquire biometric information of the user based on reflection light of the light of the preset intensity emitted from the display, where the reflection light is acquired using the image sensor.

Other aspects, advantages, and salient features of the disclosure will become apparent to those skilled in the art from the following detailed description, which, taken in conjunction with the annexed drawings, discloses an embodiment of the disclosure.

BRIEF DESCRIPTION OF THE DRAWINGS

The above and other aspects, features, and advantages of certain embodiments of the disclosure will be more apparent from the following description taken in conjunction with the accompanying drawings, in which:

FIG. 5A is a view illustrating biometric information measurement using an electronic device according to an embodiment;

FIG. 5B is a view illustrating the biometric information measurement using the electronic device according to an embodiment;

FIG. 5C is a view illustrating the biometric information measurement using the electronic device according to an embodiment;

FIG. 5D is a view illustrating the biometric information measurement using the electronic device according to an embodiment;

FIG. 5E is a view illustrating the biometric information measurement using the electronic device according to an embodiment;

FIG. 7A is a view illustrating biometric information measurement using an electronic device according to an embodiment;

FIG. 7B is a view illustrating the biometric information measurement using the electronic device according to an embodiment;

FIG. 7C is a view illustrating the biometric information measurement using the electronic device according to an embodiment;

FIG. 7D is a view illustrating the biometric information measurement using the electronic device according to an embodiment;

FIG. 7E is a view illustrating the biometric information measurement using the electronic device according to an embodiment;

FIG. 9A is a view illustrating biometric information measurement using an electronic device according to an embodiment;

FIG. 9B is a view illustrating the biometric information measurement using the electronic device according to an embodiment;

FIG. 9C is a view illustrating the biometric information measurement using the electronic device according to an embodiment;

FIG. 9D is a view illustrating the biometric information measurement using the electronic device according to an embodiment;

FIG. 9E is a view illustrating the biometric information measurement using the electronic device according to an embodiment;

FIG. 10A is a view illustrating an example of an emissive area of an electronic device according to an embodiment;

FIG. 10B is a view illustrating an example of the emissive area of the electronic device according to an embodiment;

FIG. 10C is a view illustrating an example of the emissive area of the electronic device according to an embodiment;

Throughout the drawings, like reference numerals will be understood to refer to like parts, components and structures.

DETAILED DESCRIPTION

Figure 1:
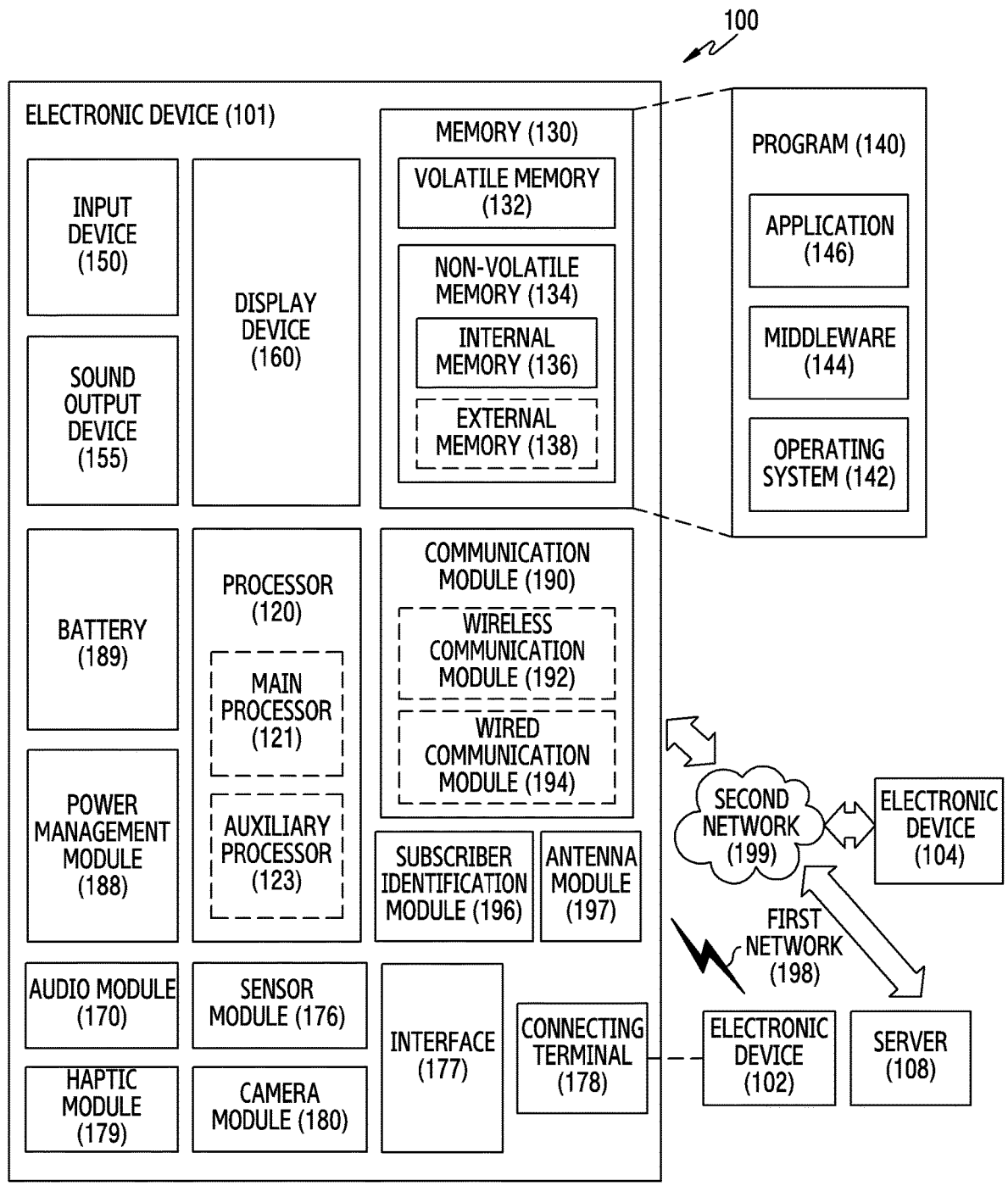
FIG. 1 illustrates a block diagram of an electronic device in a network environment according to an embodiment.

FIG. 1 is a block diagram illustrating an electronic device 101 in a network environment 100 according to an embodiment. Referring to FIG. 1, the electronic device 101 in the network environment 100 may communicate with an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input device 150, a sound output device 155, a display device 160, an audio module 170, a sensor module 176, an interface 177, a haptic module 179, a camera module 180, a power management module 188, a battery 189, a communication module 190, a subscriber identification module (SIM) 196, or an antenna module 197. In some embodiments, at least one (e.g., the display device 160 or the camera module 180) of the components may be omitted from the electronic device 101, or one or more other components may be added in the electronic device 101. In some embodiments, some of the components may be implemented as single integrated circuitry. For example, the sensor module 176 (e.g., a fingerprint sensor, an iris sensor, or an illuminance sensor) may be implemented as embedded in the display device 160 (e.g., a display).

The processor 120 may execute, for example, software (e.g., a program 140) to control at least one other component (e.g., a hardware or software component) of the electronic device 101 coupled with the processor 120, and may perform various data processing or computation. According to an example embodiment, as at least part of the data processing or computation, the processor 120 may load a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), and an auxiliary processor 123 (e.g., a graphics processing unit (GPU), an image signal processor (ISP), a sensor hub processor, or a communication processor (CP)) that is operable independently from, or in conjunction with, the main processor 121. Additionally or alternatively, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display device 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input device 150 may receive a command or data to be used by other component (e.g., the processor 120) of the electronic device 101, from the outside (e.g., a user) of the electronic device 101. The input device 150 may include, for example, a microphone, a mouse, a keyboard, or a digital pen (e.g., a stylus pen).

The sound output device 155 may output sound signals to the outside of the electronic device 101. The sound output device 155 may include, for example, a speaker or a receiver. The speaker may be used for general purposes, such as playing multimedia or playing record, and the receiver may be used for incoming calls. According to an embodiment, the receiver may be implemented as separate from, or as part of the speaker.

The display device 160 may visually provide information to the outside (e.g., a user) of the electronic device 101. The display device 160 may include, for example, a display, a hologram device, or a projector and control circuitry to control a corresponding one of the display, hologram device, and projector. According to an embodiment, the display device 160 may include touch circuitry adapted to detect a touch, or sensor circuitry (e.g., a pressure sensor) adapted to measure the intensity of force incurred by the touch.

The audio module 170 may convert a sound into an electrical signal and vice versa. According to an embodiment, the audio module 170 may obtain the sound via the input device 150, or output the sound via the sound output device 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to an example embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The antenna module 197 may transmit or receive a signal or power to or from the outside (e.g., the external electronic device) of the electronic device 101. According to an embodiment, the antenna module 197 may include an antenna including a radiating element composed of a conductive material or a conductive pattern formed in or on a substrate (e.g., printed circuit board (PCB)). According to an embodiment, the antenna module 197 may include a plurality of antennas. In such a case, at least one antenna appropriate for a communication scheme used in the communication network, such as the first network 198 or the second network 199, may be selected, for example, by the communication module 190 (e.g., the wireless communication module 192) from the plurality of antennas. The signal or the power may then be transmitted or received between the communication module 190 and the external electronic device via the selected at least one antenna. According to an embodiment, another component (e.g., a radio frequency integrated circuit (RFIC)) other than the radiating element may be additionally formed as part of the antenna module 197.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 and 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, or client-server computing technology may be used, for example.

Figure 2:
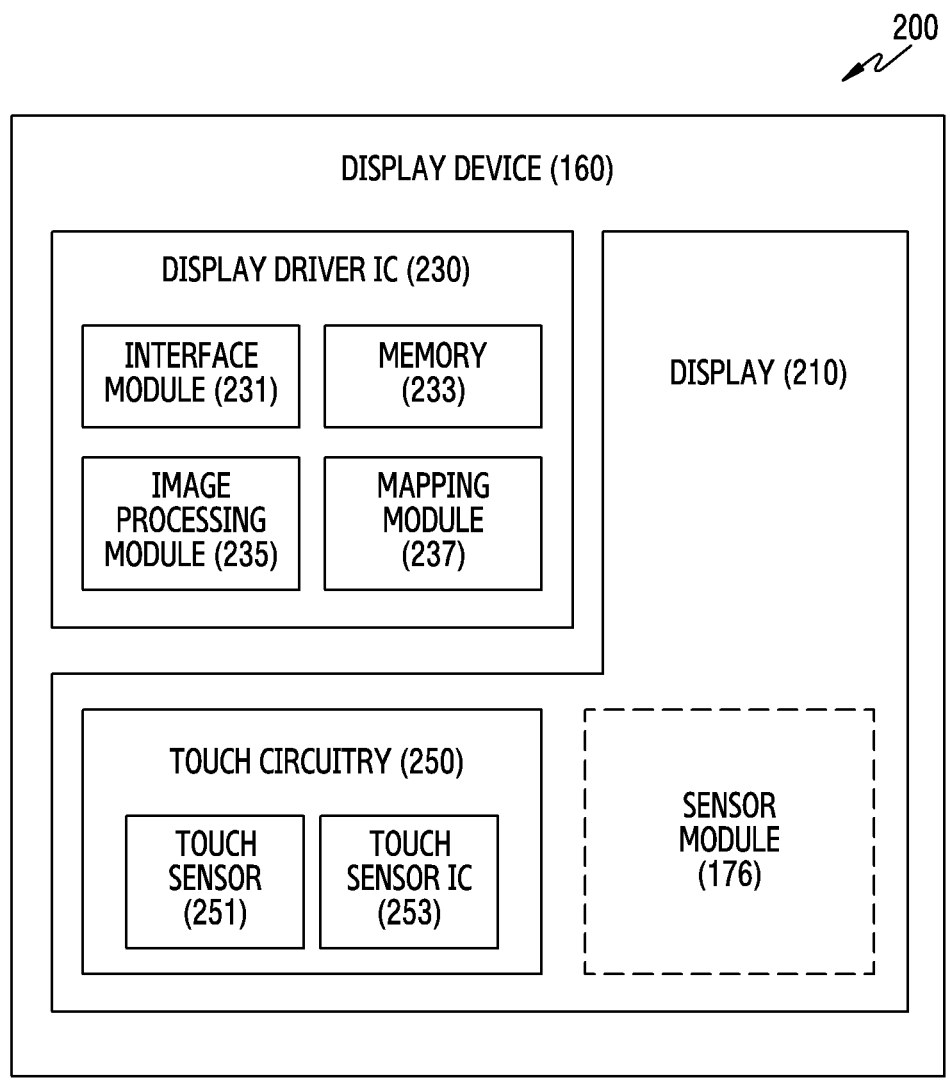
FIG. 2 illustrates a block diagram of a display device according to an embodiment.

FIG. 2 is a block diagram 200 illustrating the display device 160 according to an embodiment. Referring to FIG. 2, the display device 160 may include a display 210 and a display driver integrated circuit (DDI) 230 to control the display 210. The DDI 230 may include an interface module 231, memory 233 (e.g., buffer memory), an image processing module 235, or a mapping module 237. The DDI 230 may receive image information that contains image data or an image control signal corresponding to a command to control the image data from another component of the electronic device 101 via the interface module 231. For example, according to an embodiment, the image information may be received from the processor 120 (e.g., the main processor 121 (e.g., an application processor)) or the auxiliary processor 123 (e.g., a graphics processing unit) operated independently from the function of the main processor 121. The DDI 230 may communicate, for example, with touch circuitry 150 or the sensor module 176 via the interface module 231. The DDI 230 may also store at least part of the received image information in the memory 233, for example, on a frame by frame basis.

The image processing module 235 may perform preprocessing or post-processing (e.g., adjustment of resolution, brightness, or size) with respect to at least part of the image data. According to an embodiment, the pre-processing or post-processing may be performed, for example, based at least in part on one or more characteristics of the image data or one or more characteristics of the display 210.

The mapping module 237 may generate a voltage value or a current value corresponding to the image data pre-processed or post-processed by the image processing module 235. According to an embodiment, the generating of the voltage value or current value may be performed, for example, based at least in part on one or more attributes of the pixels (e.g., an array, such as an RGB stripe or a pentile structure, of the pixels, or the size of each subpixel). At least some pixels of the display 210 may be driven, for example, based at least in part on the voltage value or the current value such that visual information (e.g., a text, an image, or an icon) corresponding to the image data may be displayed via the display 210.

According to an embodiment, the display device 160 may further include the touch circuitry 250. The touch circuitry 250 may include a touch sensor 251 and a touch sensor IC 253 to control the touch sensor 251. The touch sensor IC 253 may control the touch sensor 251 to sense a touch input or a hovering input with respect to a certain position on the display 210. To achieve this, for example, the touch sensor 251 may detect (e.g., measure) a change in a signal (e.g., a voltage, a quantity of light, a resistance, or a quantity of one or more electric charges) corresponding to the certain position on the display 210. The touch circuitry 250 may provide input information (e.g., a position, an area, a pressure, or a time) indicative of the touch input or the hovering input detected via the touch sensor 251 to the processor 120. According to an embodiment, at least part (e.g., the touch sensor IC 253) of the touch circuitry 250 may be formed as part of the display 210 or the DDI 230, or as part of another component (e.g., the auxiliary processor 123) disposed outside the display device 160.

According to an embodiment, the display device 160 may further include at least one sensor (e.g., a fingerprint sensor, an iris sensor, a pressure sensor, or an illuminance sensor) of the sensor module 176 or a control circuit for the at least one sensor. In such a case, the at least one sensor or the control circuit for the at least one sensor may be embedded in one portion of a component (e.g., the display 210, the DDI 230, or the touch circuitry 150)) of the display device 160. For example, when the sensor module 176 embedded in the display device 160 includes a biometric sensor (e.g., a fingerprint sensor), the biometric sensor may obtain biometric information (e.g., a fingerprint image) corresponding to a touch input received via a portion of the display 210. As another example, when the sensor module 176 embedded in the display device 160 includes a pressure sensor, the pressure sensor may obtain pressure information corresponding to a touch input received via a partial or whole area of the display 210. According to an embodiment, the touch sensor 251 or the sensor module 176 may be disposed between pixels in a pixel layer of the display 210, or over or under the pixel layer.

Figure 3:
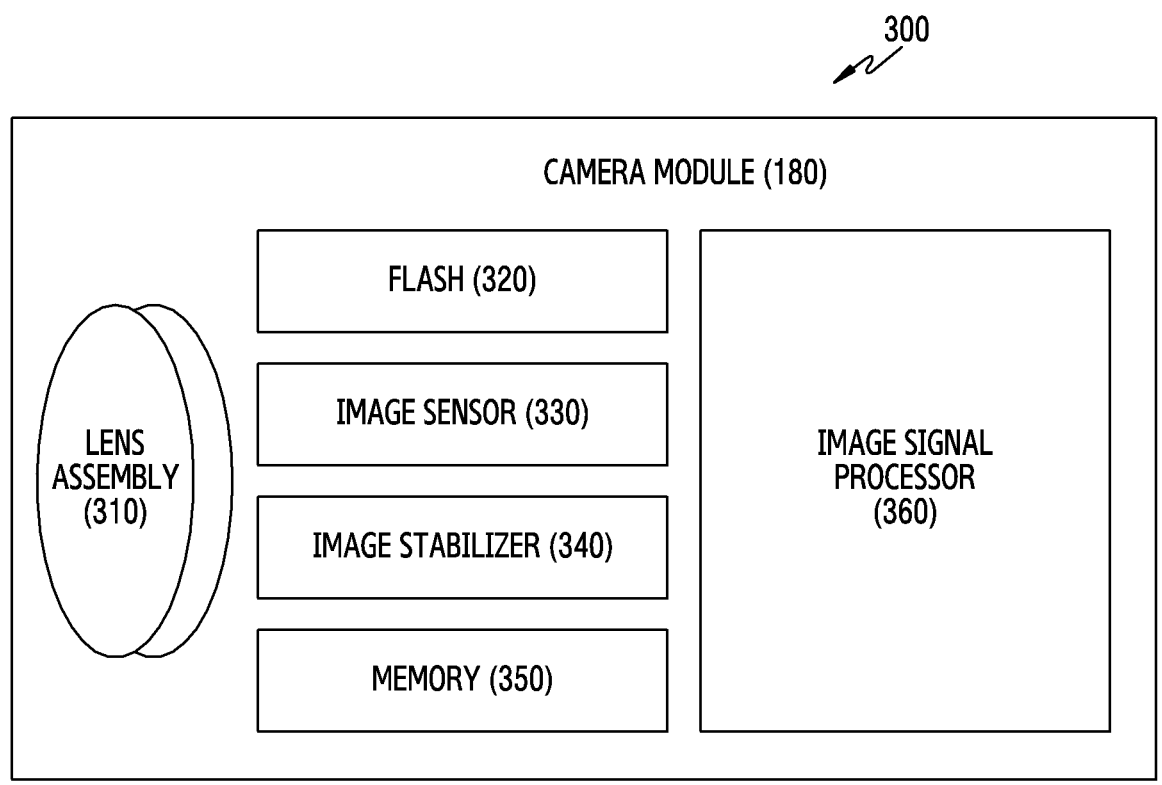
FIG. 3 illustrates a block diagram of a camera module according to an embodiment.

FIG. 3 is a block diagram 300 illustrating the camera module 180 according to an embodiment. Referring to FIG. 3, the camera module 180 may include a lens assembly 310, a flash 320, an image sensor 330, an image stabilizer 340, memory 350 (e.g., buffer memory), or an image signal processor 360. The lens assembly 310 may collect light emitted or reflected from an object whose image is to be taken. The lens assembly 310 may include one or more lenses. According to an embodiment, the camera module 180 may include a plurality of lens assemblies 310. In such a case, the camera module 180 may form, for example, a dual camera, a 360-degree camera, or a spherical camera. Some of the plurality of lens assemblies 310 may have the same lens attribute (e.g., view angle, focal length, autofocusing, f number, or optical zoom), or at least one lens assembly may have one or more lens attributes different from those of another lens assembly. The lens assembly 310 may include, for example, a wide-angle lens or a telephoto lens.

The flash 320 may emit light that is used to reinforce light reflected from an object. According to an embodiment, the flash 320 may include one or more light emitting diodes (LEDs) (e.g., a red-green-blue (RGB) LED, a white LED, an infrared (IR) LED, or an ultraviolet (UV) LED) or a xenon lamp. The image sensor 330 may obtain an image corresponding to an object by converting light emitted or reflected from the object and transmitted via the lens assembly 310 into an electrical signal. According to an embodiment, the image sensor 330 may include one selected from image sensors having different attributes, such as a RGB sensor, a black-and-white (BW) sensor, an IR sensor, or a UV sensor, a plurality of image sensors having the same attribute, or a plurality of image sensors having different attributes. Each image sensor included in the image sensor 330 may be implemented using, for example, a charged coupled device (CCD) sensor or a complementary metal oxide semiconductor (CMOS) sensor.

The image stabilizer 340 may move the image sensor 330 or at least one lens included in the lens assembly 310 in a particular direction, or control an operational attribute (e.g., adjust the read-out timing) of the image sensor 330 in response to the movement of the camera module 180 or the electronic device 101 including the camera module 180. This allows compensating for at least part of a negative effect (e.g., image blurring) by the movement on an image being captured. According to an embodiment, the image stabilizer 340 may sense such a movement by the camera module 180 or the electronic device 101 using a gyro sensor (not shown) or an acceleration sensor (not shown) disposed inside or outside the camera module 180. According to an embodiment, the image stabilizer 340 may be implemented, for example, as an optical image stabilizer.

The memory 350 may store, at least temporarily, at least part of an image obtained via the image sensor 330 for a subsequent image processing task. For example, if image capturing is delayed due to shutter lag or multiple images are quickly captured, a raw image obtained (e.g., a Bayer-patterned image, a high-resolution image) may be stored in the memory 350, and its corresponding copy image (e.g., a low-resolution image) may be previewed via the display device 160. Thereafter, if a specified condition is met (e.g., by a user's input or system command), at least part of the raw image stored in the memory 350 may be obtained and processed, for example, by the image signal processor 360. According to an embodiment, the memory 350 may be configured as at least part of the memory 130 or as a separate memory that is operated independently from the memory 130.

The image signal processor 360 may perform one or more image processing with respect to an image obtained via the image sensor 330 or an image stored in the memory 350. The one or more image processing may include, for example, depth map generation, three-dimensional (3D) modeling, panorama generation, feature point extraction, image synthesizing, or image compensation (e.g., noise reduction, resolution adjustment, brightness adjustment, blurring, sharpening, or softening). Additionally or alternatively, the image signal processor 360 may perform control (e.g., exposure time control or read-out timing control) with respect to at least one (e.g., the image sensor 330) of the components included in the camera module 180. An image processed by the image signal processor 360 may be stored back in the memory 350 for further processing, or may be provided to an external component (e.g., the memory 130, the display device 160, the electronic device 102, the electronic device 104, or the server 108) outside the camera module 180. According to an embodiment, the image signal processor 360 may be configured as at least part of the processor 120, or as a separate processor that is operated independently from the processor 120. If the image signal processor 360 is configured as a separate processor from the processor 120, at least one image processed by the image signal processor 360 may be displayed, by the processor 120, via the display device 160 as it is or after being further processed.

According to an embodiment, the electronic device 101 may include a plurality of camera modules 180 having different attributes or functions. In such a case, at least one of the plurality of camera modules 180 may form, for example, a wide-angle camera and at least another of the plurality of camera modules180 may form a telephoto camera. Similarly, at least one of the plurality of camera modules 180 may form, for example, a front camera and at least another of the plurality of camera modules180 may form a rear camera.

The electronic device according to an embodiment may be one of various types of electronic devices. The electronic devices may include, for example, and without limitation, a portable communication device (e.g., a smartphone), a computer device, a portable multimedia device, a portable medical device, a camera, a wearable device, a home appliance, or the like. According to an embodiment of the disclosure, the electronic devices are not limited to those described above.

It should be appreciated that an embodiment of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), the element may be coupled with the other element directly (e.g., wiredly), wirelessly, or via a third element.

As used herein, the term "module" may include a unit implemented in hardware, software, or firmware, or any combination thereof, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

An embodiment as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a compiler or a code executable by an interpreter. The machine-readable storage medium may be provided in the form of a non-transitory storage medium. Wherein, the "non-transitory" storage medium is a tangible device, and may not include a signal (e.g., an electromagnetic wave), but this term does not differentiate between where data is semi-permanently stored in the storage medium and where the data is temporarily stored in the storage medium.

According to an embodiment, a method according to an embodiment of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to an embodiment, each component (e.g., a module or a program) of the above-described components may include a single entity or multiple entities. According to an embodiment, one or more of the above-described components may be omitted, or one or more other components may be added. Alternatively or additionally, a plurality of components (e.g., modules or programs) may be integrated into a single component. In such a case, according to an embodiment, the integrated component may still perform one or more functions of each of the plurality of components in the same or similar manner as they are performed by a corresponding one of the plurality of components before the integration. According to an embodiment, operations performed by the module, the program, or another component may be carried out sequentially, in parallel, repeatedly, or heuristically, or one or more of the operations may be executed in a different order or omitted, or one or more other operations may be added.

Figures 4A, 4B:
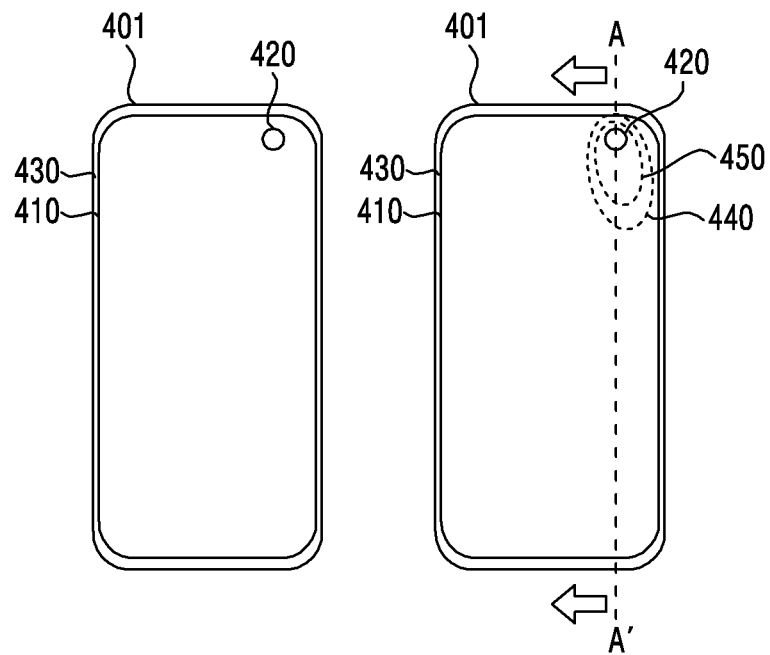
FIG. 4A is a view illustrating an electronic device according to an embodiment.
FIG. 4B is a view illustrating the electronic device according to an embodiment.
Figure 4C:
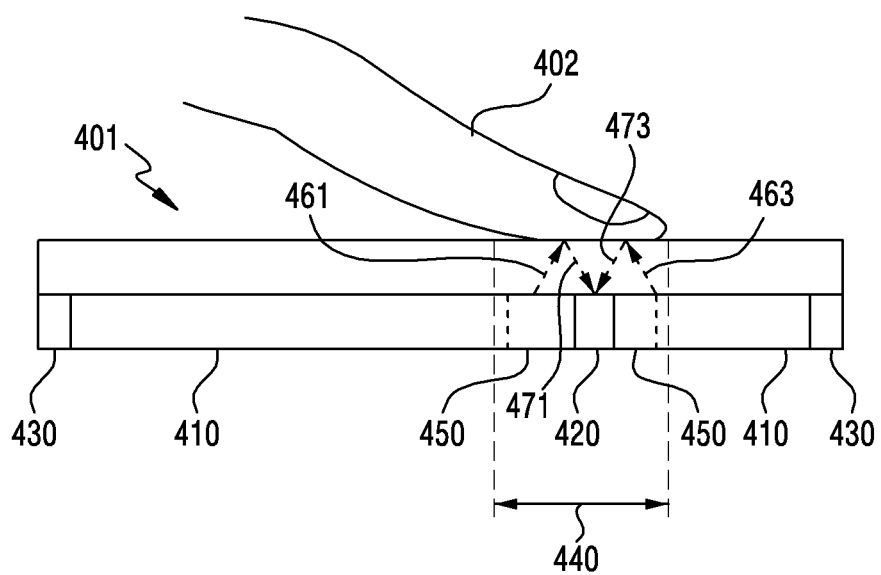
FIG. 4C is a view illustrating the electronic device according to an embodiment.

FIGS. 4A, 4B, and 4C are views illustrating an electronic device 401 according to an embodiment. FIG. 4A illustrates the electronic device 401 according to an embodiment. FIG. 4B is a view illustrating when the electronic device 401 acquires biometric information using the light of a display 410 according to an embodiment. FIG. 4C illustrates a side view of the electronic device 401 according to an embodiment, which is taken along a reference line A-A' in FIG. 4B. In an embodiment, the electronic device 401 of FIG. 4 may correspond to the electronic device 101 of FIG. 1. In an embodiment, the electronic device 401 of FIG. 4 shall be described by referring to the configuration of the electronic device 101 of FIG. 1.

Referring to FIG. 4A, in an embodiment, the electronic device 401 may include the display 410 and/or a camera 420. In an embodiment, the display 410 and the camera 420 may correspond to the display 160 and the camera 180 of FIG. 1 respectively. In an embodiment, the electronic device 401 may further include a processor (e.g., the processor 120 of FIG. 1). The processor 120 may include a microprocessor or any suitable type of processing circuitry, such as one or more general-purpose processors (e.g., ARM-based processors), a Digital Signal Processor (DSP), a Programmable Logic Device (PLD), an Application-Specific Integrated Circuit (ASIC), a Field-Programmable Gate Array (FPGA), a Graphical Processing Unit (GPU), a video card controller, etc. In addition, it would be recognized that when a general purpose computer accesses code for implementing the processing shown herein, the execution of the code transforms the general purpose computer into a special purpose computer for executing the processing shown herein. Certain of the functions and steps provided in the Figures may be implemented in hardware, software or a combination of both and may be performed in whole or in part within the programmed instructions of a computer. No claim element herein is to be construed under the provisions of 35 U.S.C. § 112(f), unless the element is expressly recited using the phrase "means for." In addition, an artisan understands and appreciates that a "processor" or "microprocessor" may be hardware in the claimed disclosure. Under the broadest reasonable interpretation, the appended claims are statutory subject matter in compliance with 35 U.S.C. § 101.

Referring to FIG. 4A, in an embodiment, the display 410 may be exposed through, for example, most of a front plate 430. In an embodiment, a recess or an opening may be formed in part of the screen display area of the display 410, and another electronic part, for example, the camera 420, a proximity sensor (not shown), and/or a light sensor (not shown), may be aligned with the recess or the opening.

In an embodiment, the processor (e.g., the processor 120 of FIG. 1) may display a first user interface on the display 410 for receiving an input for acquiring user's biometric information. In an embodiment, the first user interface may receive an input (e.g., a touch input) for selecting the type of the user's biometric information to measure while a biometric information measurement application is running. In an embodiment, the processor 120 may identify the type of the user's biometric information to measure based on the input received through the first user interface. In an embodiment, the first user interface may be generated by another running application that is not the biometric information measurement application. In an embodiment, the input for acquiring the user's biometric information may include a touch which covers the camera 420 with a user's finger 402. In an embodiment, the biometric information may include, but is not limited to, heart rate, oxygen saturation, stress index, blood pressure, blood sugar, tissue hydration, tissue dehydration, fingerprint, or a combination thereof.

Referring to FIG. 4B and FIG. 4C, in an embodiment, the processor 120 may receive the input for acquiring the user's biometric information through the display 410. In an embodiment, the processor 120 may detect the touch which covers the camera 420 with the user's finger 402 on the display 410.

In an embodiment, if the touch that covers the camera 420 with the user's finger 402 is detected, the processor 120 may display a second user interface on the display 410. In an embodiment, the second user interface may be associated with the measurement of the user's biometric information while the biometric information measurement application is running.

In an embodiment, while displaying the second user interface, the processor 120 may set an emissive area 450 in response to detecting a touch area 440 from the touch that is covering the camera 420 with the user's finger 402, and control the display 410 to emit lights 461 and 463 from the set emissive area 450. In an embodiment, the touch area 440 may be detected by using a touch sensor (not shown) and/or a pressure sensor (not shown) of the display 410. In an embodiment, the intensity of the lights 461 and 463 emitted from the emissive area 450 may be higher than the intensity of a light emitted from other areas of the second user interface. In an embodiment, the intensity of the lights 461 and 463 emitted from the emissive area 450 may be, for example, higher than the light intensity from the display 410 when the first user interface is displayed. Alternatively, the intensity of the lights 461 and 463 emitted from the emissive area 450 may be higher than or equal to the light intensity from the display 410 when the first user interface is displayed. In an embodiment, while the first user interface is displayed, light may be emitted from the display 410 at a first intensity, and the lights 461 and 463 may be emitted from the emissive area 450 at a second intensity which is higher than the first intensity.

In an embodiment, the processor 120 may set the emissive area 450 within the touch area 440 that corresponds to the touch input that is covering the camera 420 with the finger 402. In an embodiment, the processor 120 may set the edge of the emissive area 450 to be within a set distance from the camera 420 based on the touch area 440 which covers the camera 420 with the finger 402. In an embodiment, the processor 120 may set the size of the emissive area 450 to correspond to the touch area 440. In an embodiment, the boundary of the emissive area 450 may be within the boundary of the touch area 440. In an embodiment, the processor 120 may change the size and/or the boundary of the emissive area 450 as the touch area 440 changes.

In an embodiment, the processor 120 may set the emissive area 450 based on the type of the biometric information to be acquired. In an embodiment, the processor 120 may adjust the shape of the emissive area 450 and/or the position of the emissive area 450 on the display 410 in response to the type of the biometric information to be acquired. In an embodiment, information relating to the shape of the emissive area 450, the position of the emissive area 450 on the display 410, or their combination may be preset in a memory (e.g., the memory 130 of FIG. 1) per type of the biometric information to be acquired. In an embodiment, the shape of the emissive area 450 may include a polygon, a circle, an oval, or a combination thereof. In an embodiment, the position of the emissive area 450 may include a position away from the camera 420 by a preset distance on the display 410, a position surrounding the camera 420, or a combination thereof.

In an embodiment, the processor 120 may adjust the color of the lights 461 and 463, the intensity of the lights 461 and 463, or a combination thereof, in response to the type of the biometric information to acquire. In an embodiment, the processor 120 may adjust the color of the lights 461 and 463, the intensity of the lights 461 and 463, or a combination thereof, in response to the touch area of the finger 402. In an embodiment, the processor 120 may adjust the intensity of the lights 461 and 463 to increase as the touch area of the finger 402 narrows. In an embodiment, information relating to the color of the lights 461 and 463, the intensity of the lights 461 and 463, or their combination per the type of the biometric information to be acquired may be preset in the memory (e.g., the memory 130 of FIG. 1).

Referring to FIG. 4B and FIG. 4C, in an embodiment, the processor 120 may receive reflection lights 471 and 473 of the lights 461 and 463 emitted from the emissive area 450, through the camera 420. In an embodiment, the processor 120 may acquire the user's biometric information, based on the received reflection lights 471 and 473.

In an embodiment, the processor 120 may reset the emissive area 450 based on the reflection lights 471 and 473. In an embodiment, if asymmetry for a reference direction of an image acquired based on the reflection lights 471 and 473 is identified, the processor 120 may reset the emissive area 450, based on the degree of the asymmetry for the reference direction of the image. In an embodiment, the processor 120 may reset the emissive area 450 to generate a symmetric image acquired based on the reflection lights 471 and 473. In an embodiment, the processor 120 may acquire the user's biometric information based on the reset emissive area.

In an embodiment, the lights 461 and 463 are the lights of the display 410 by way of example, but the lights 461 and 463 may be emitted by a light source which emits infrared light (e.g., an infrared light emitting diode (LED)). In an embodiment, if the lights 461 and 463 are the infrared lights, the camera 420 may be a time of flight (TOF) sensor or a fingerprint sensor.

FIGS. 5A through 5E are views each illustrating biometric information measurement using an electronic device 501 according to an embodiment. FIGS. 6A through 6F are views each illustrating an example of an emissive area of an electronic device 601 according to an embodiment. In an embodiment, the electronic device 501 of FIG. 5 or the electronic device 601 of FIG. 6 may correspond to the electronic device 101 of FIG. 1 or the electronic device 401 of FIG. 4. In an embodiment, FIGS. 5A through 5E and FIGS. 6A through 6F are described by referring to the configuration of the electronic device 101 of FIG. 1.

In an embodiment, referring to FIGS. 5A through 5E, a camera 520 of the electronic device 501 may overlap the display 510, if the electronic device 501 is viewed from a first direction (e.g., a front direction of the electronic device 501). In an embodiment, the overlapping area of the camera 520 of the electronic device 501 on the display 510 may not include a light emitting device of the display 510. In an embodiment, the display 510 may be exposed through, for example, most of the front plate 530.

In an embodiment, referring to FIG. 5A, a processor (e.g., the processor 120) may display a first user interface 511 on the display 510. In an embodiment, the first user interface 511 may receive an input (e.g., a touch input) for selecting the type of user's biometric information to measure while, for example, a biometric information measurement application is running. In an embodiment, the first user interface 511 may be generated by another running application than is not the biometric information measurement application.

In an embodiment, referring to FIG. 5B, the processor 120 may identify a touch covering the camera 520 with a user's finger (e.g., the finger 402 of FIG. 4), while displaying the first user interface 511 on the display 510. In an embodiment, if the touch covering the camera 520 is identified, the processor 120 may display a second user interface 513 which is different from the first user interface 511 on the display 510.

In an embodiment, the processor 120 may identify the touch covering the camera 520, based on a touch area detected by a touch sensor (not shown) of the display 510 that corresponds to a touch area 540 of the finger 402. In an embodiment, if the detected touch area surrounds the camera 520, the processor 120 may identify that the touch is covering the camera 520. In an embodiment, if the touch of the finger 402 is detected, the processor 120 may identify the touch covering the camera 520 based on an image acquired through the camera 520. In an embodiment, in response to the touch input in a preset area (e.g., a preset area to surround the camera 520) of the display 510, the processor 120 may enable the camera 520 and identify the touch covering the camera 520 based on the image acquired through the camera 520.

In an embodiment, if the touch covering the camera 520 is identified, the processor 120 may identify whether the camera 520 is completely covered with the finger 402. In an embodiment, the processor 120 may identify whether the camera 520 is completely covered based on light acquired through an image sensor (not shown) of the camera 520. In an embodiment, if the light acquired through the image sensor (not shown) of the camera 520 includes light other than the reflection light of the light emitted from the display 510, the processor 120 may identify that the camera 520 is not completely covered with the finger 402. In an embodiment, if the light acquired through the image sensor (not shown) of the camera 520 does not include light other than the reflection light of the light emitted from the display 510, the processor 120 may identify that the camera 520 is completely covered with the finger 402.

In an embodiment, if the camera 520 is completely covered with the finger 402, the processor 120 may display the second user interface 513 for biometric measurement as shown in FIG. 5C. In an embodiment, if the camera 520 is not completely covered with the finger 402, the processor 120 may display a third user interface 515 including an indicator 514 which guides the user to retouch the display 510 with his or her finger 402 as shown in FIG. 5D. In an embodiment, the second user interface 513 may be displayed when measuring the user's biometric information while the biometric information measurement application is running. In an embodiment, the third user interface 515 may indicate to the user that retouch is required in order for biometric information to be measured.

In an embodiment, referring to FIG. 5C, the processor 120 may display the second user interface 513 on the display 510. In an embodiment, the processor 120 may set part of the second user interface 513 as an emissive area 550. In an embodiment, the processor 120 may set the emissive area 550 based on the touch area 540 of the finger 402. In an embodiment, the processor 120 may set the emissive area 550 so that its boundary is within the touch area 540 of the finger 402. In an embodiment, the processor 120 may set the emissive area 550 to surround the camera 520. In an embodiment, the processor 120 may determine the shape, pattern, size, position, or their combination of the emissive area 550, based on the type of the biometric information to be acquired, where the type may be selected by the user while the first user interface 511 is displayed.

In an embodiment, the processor 120 may emit preset lights (e.g., the lights 461 and 463 of FIG. 4) in the emissive area 550 on the display 510. In an embodiment, the processor 120 may determine the color, intensity, or their combination of the lights 461 and 463, based on the type of the biometric information to be acquired. In an embodiment, the processor 120 may determine the color, intensity, or their combination of the lights 461 and 463, while the first user interface 511 is displayed.

In an embodiment, the processor 120 may emit the lights 461 and 463 in the emissive area 550 on the display 510, and measure the user's biometric information, based on the reflection lights 471 and 473 of the lights 461 and 463 acquired through the camera 520.

While the emissive area 550 of FIG. 5C is shown in this example in a ring shape, the instant disclosure is not so limited and the emissive area 550 may adopt various shapes. In an embodiment, referring to FIG. 6A, the electronic device 601 may include two or more emissive areas 651 and 652 on the display 610, where the display 610 is exposed through most of a front plate 630 of the electronic device 601. In an embodiment, the emissive areas 651 and 652 collectively may have a circular shape. In an embodiment, the emissive areas 651 and 652 may be disposed symmetrically around the center of a camera 620, by way of example. Alternatively, the emissive areas 651 and 652 may be disposed asymmetrically around the center of the camera 620.

In an embodiment, the processor 120 may control to illuminate the emissive areas 651 and 652 at different times. In an embodiment, the processor 120 may illuminate the emissive area 651 in a first time duration, and illuminate the emissive area 652 in a second time duration after the expiration of the first time duration. In an embodiment, the first time duration and the second time duration may each be a time duration for the biometric measurement.

In an embodiment, the processor 120 may control to illuminate the emissive areas 651 and 652 in different colors. In an embodiment, the processor 120 may emit light of a first color (e.g., red) from the emissive area 651, and emit light of a second color (e.g., green) from the emissive area 652 by way of example. Alternatively, the processor 120 may control to illuminate the emissive areas 651 and 652 in the same color.

In an embodiment, the processor 120 may control to emit light of the first color (e.g., red) from the emissive areas 651 and 652 in the first time duration, and to emit light of the second color (e.g., green) from the emissive areas 651 and 652 in the second time duration. In an embodiment, the processor 120 may control the emissive areas 651 and 652 to emit light in a color (e.g., yellow) mixed from the first color (e.g., red) and the second color (e.g., green).

Figures 6A, 6B, 6C:
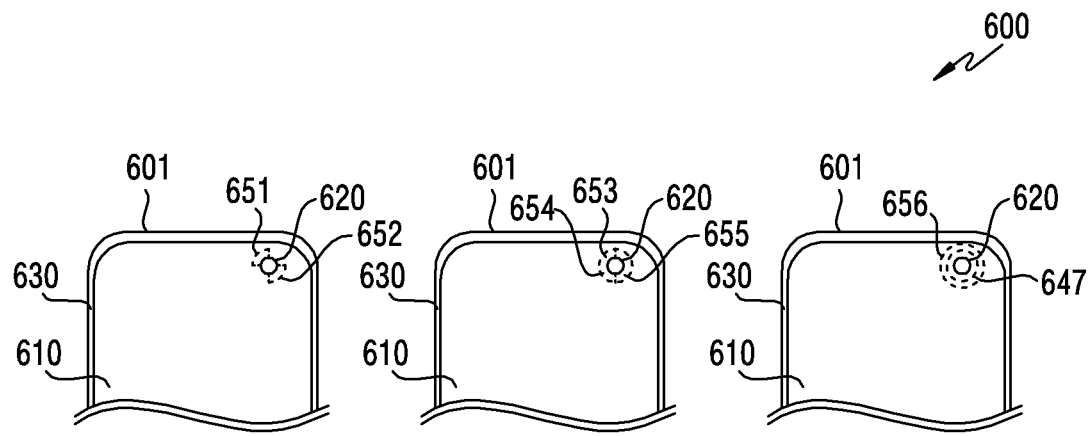
FIG. 6A is a view illustrating an example of an emissive area of an electronic device according to an embodiment.
FIG. 6B is a view illustrating an example of the emissive area of the electronic device according to an embodiment.
FIG. 6C is a view illustrating an example of the emissive area of the electronic device according to an embodiment.

In an embodiment, referring to FIG. 6B, an emissive area 653 of the display 610 exposed through most of the front plate 630 of the electronic device 601 may include two or more emissive subareas 654 and 655. In an embodiment, to emit the light in a preset pattern, the processor 120 may divide the emissive area 653 into two or more emissive subareas 654 and 655. In an embodiment, the processor 120 may control the display 610 to emit the light corresponding to the preset pattern from the emissive subareas 654 and 655.

In an embodiment, the processor 120 may control to illuminate the emissive subareas 654 and 655 at different times. In an embodiment, the processor 120 may control to illuminate the emissive subareas 654 and 655 in different colors.

In an embodiment, referring to FIG. 6C, emissive areas 656 and 657 of the display 610 exposed through most of the front plate 630 of the electronic device 601 may include the emissive area 657 directly adjacent to the camera 620 and the emissive area 656 in which the emissive area 657 is interposed between the emissive area 656 and the camera 620. In an embodiment, the processor 120 may control to illuminate the emissive areas 656 and 657 at different times. In an embodiment, the processor 120 may control to illuminate the emissive areas 656 and 657 in different colors. In an embodiment, the processor 120 may control the emissive areas 656 and 657 so that light sources closer to the camera 620 emit light of relatively shorter wavelengths. For example, the emissive area 656, which is farther from the camera 620, may emit light of the first color (e.g., red), and the emissive area 657, which is closer to the camera 620, may emit light of the second color (e.g., green).

In an embodiment, the processor 120 may control to illuminate the emissive areas 656 and 657 with different intensities. In an embodiment, the processor 120 may control to illuminate the emissive area 656 with light of a first intensity, and to illuminate the emissive area 657 with light of a second intensity. In different embodiments, the first intensity may be higher or lower than the second intensity.

Figures 6D, 6E, 6F:
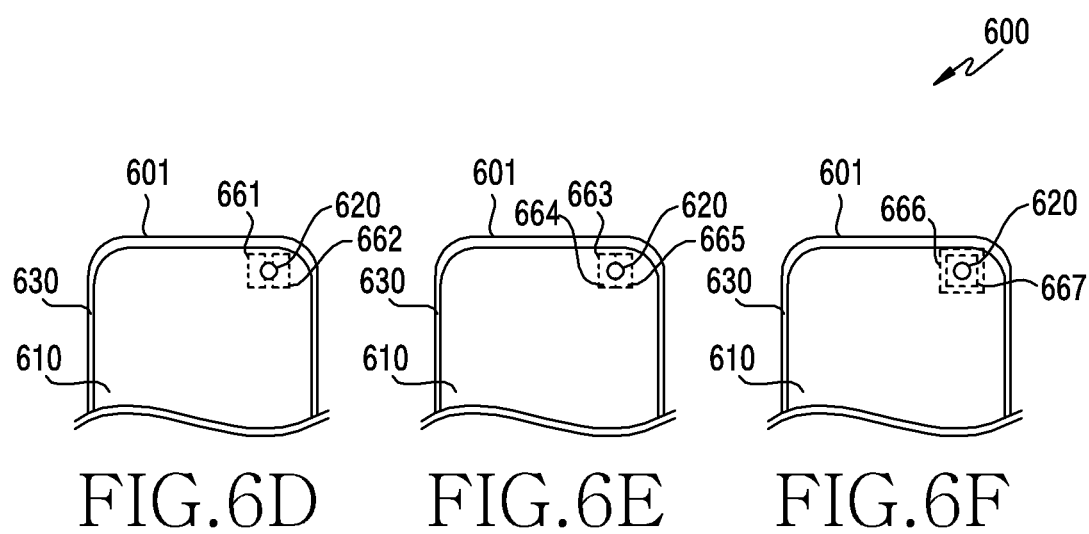
FIG. 6D is a view illustrating an example of the emissive area of the electronic device according to an embodiment.
FIG. 6E is a view illustrating an example of the emissive area of the electronic device according to an embodiment.
FIG. 6F is a view illustrating an example of the emissive area of the electronic device according to an embodiment.

In an embodiment, referring to FIG. 6D, two or more emissive areas 661 and 662 of the display 610 exposed through most of the front plate 630 of the electronic device 601 may be configured. In an embodiment, the emissive areas 661 and 662 together may form a quadrangular shape.

In an embodiment, referring to FIG. 6E, a quadrangular emissive area 663 of the display 610 exposed through most of the front plate 630 of the electronic device 601 may include two or more emissive subareas 664 and 665.

In an embodiment, referring to FIG. 6F, emissive areas 666 and 667 of the display 610 of the front plate 630 of the electronic device 601 may include the quadrangular emissive area 667 directly adjacent to the camera 620 and the quadrangular emissive area 666, in which the emissive area 667 is interposed between the quadrangular emissive area 666 and the camera 620.

The emissive areas 651, 652, 653, 656, 657, 661, 662, 663, 666, and 667 are shown here either as circular or quadrangular. However, these are only examples, and the emissive areas may be additional shapes such as polygons.

In an embodiment, referring to FIG. 5D, if the processor 120 identifies that the camera 520 is not completely covered with the finger 402, the processor 120 may display the indicator 514 on the third user interface 515 which guides the user to retouch the display 510 with his or her finger 402. In an embodiment, the indicator 514 may be an image object in a shape indicating the camera 520 by way of example. The indicator 514 may include a phrase, an image, or their combination, for requesting the retouch.

In an embodiment, the processor 120 may determine the position of the indicator 514, based on the position of the light other than the reflection light acquired through the image sensor (not shown) of the camera 520. The position of the light other than the reflection light may be a position corresponding to an area exposed to the light other than the reflection light. In an embodiment, if the position of the light other than the reflection light is in a first direction from the center of the camera 520, for example, the processor 120 may determine the position of the indicator 514 to be a position that is a set distance in the first direction away from a preset reference position. In an embodiment, the processor 120 may determine the set distance in response to the area exposed to the light other than the reflection light on the image acquired through the image sensor (not shown) of the camera 520. In an embodiment, the processor 120 may determine the set distance in response to the width of the area exposed to the light other than the reflection light.

In an embodiment, referring to FIG. 5E, if the indicator 514 is displayed and then the touch covering the camera 520 is identified, the processor 120 may identify whether the camera 520 is completely covered with the finger 402. In an embodiment, if it is identified that the camera 520 is completely covered by the retouch of the finger 402, the processor 120 may store position information of the indicator 514 in memory (e.g., the memory 130 of FIG. 1).

In an embodiment, if the camera 520 is completely covered by the retouch of the finger 402, the processor 120 may display the second user interface 513 for the biometric measurement as shown in FIG. 5C. In an embodiment, if the camera 520 is not completely covered by the retouch of the finger 402, the processor 120 may display again the third user interface 515 including the indicator 514 that guides the user to retouch the display 510 as shown in FIG. 5D.

In an embodiment, the processor 120 may emit the lights 461 and 463 from the emissive area of the display 510 after the retouch of the finger 402 while displaying the second user interface 513, and measure the user's biometric information, based on the reflection lights 471 and 473 of the lights 461 and 463 acquired through the camera 520.

In an embodiment, while displaying the third user interface 515, the processor 120 may redisplay the indicator 514 which requests the retouch of the finger 402. In an embodiment, the processor 120 may display the indicator 514 at a redetermined position based on the touch area 541 of the finger 402.

FIGS. 7A through 7E are views each illustrating biometric information measurement using an electronic device 701 according to an embodiment. FIGS. 8A through 8G are views each illustrating an example of an emissive area of an electronic device 801 according to an embodiment. In an embodiment, the electronic device 701 of FIG. 7 or the electronic device 801 of FIG. 8 may correspond to the electronic device 101 of FIG. 1 or the electronic device 401 of FIG. 4. In an embodiment, FIGS. 7A through 7E and FIGS. 8A through 8G are described by referring to the configuration of the electronic device 101 of FIG. 1. Redundant descriptions of FIGS. 5A through 5E and FIGS. 6A through 6F shall be omitted in the descriptions of FIGS. 7A through 7E and FIGS. 8A through 8G.

A display 710 and a camera 720 of FIGS. 7A through 7E may overlap each other, if the user views the electronic device 701 in a first direction (e.g., a front direction of the electronic device 701). In an embodiment, a light emitting device of the display 570 may be disposed in the overlapping area of the camera 720 of the electronic device 701 in the display 710. In an embodiment, the display 710 may be exposed through, for example, most of a front plate 730.

In an embodiment, if the camera 720 is disabled, the user may not be able to see the camera 720. In an embodiment, if the camera 720 is disabled, the light emitting device of the overlapping area of the camera 720 in the display 710 may emit light. Alternatively, if the camera 720 is enabled, the user may be able to see the camera 720. In an embodiment, if the camera 720 is enabled, the light emitting device of the overlapping area of the camera 720 in the display 710 may not emit light.

In an embodiment, referring to FIG. 7A, a processor (e.g., the processor 120) may display a first user interface 711 on the display 710.

In an embodiment, referring to FIG. 7B, the processor 120 may identify a touch covering the camera 720 with a user's finger (e.g., the finger 402 of FIG. 4), while the first user interface 711 is displayed on the display 710. In an embodiment, if the touch covering the camera 720 is identified, the processor 120 may display a second user interface 713 which is different from the first user interface 711 on the display 710.

In an embodiment, the processor 120 may identify the touch covering the camera 720, based on a touch area detected by a touch sensor (not shown) of the display 710 that corresponds to a touch area 740 of the finger 402. In an embodiment, if the detected touch area corresponds to the overlapping area of the camera 720 in the display 710, the processor 120 may identify the touch covering the camera 720. In an embodiment, if the detected touch area surrounds the camera 720, the processor 120 may identify the touch covering the camera 720. In an embodiment, if the touch of the finger 402 is detected, the processor 120 may identify the touch covering the camera 720 based on an image acquired through the camera 720. In an embodiment, in response to the touch input in a preset area (e.g., a preset area to surround the camera 720) of the display 710, the processor 120 may enable the camera 720 and identify the touch covering the camera 720 based on the image acquired through the camera 720.

In an embodiment, if the touch covering the camera 720 is identified, the processor 120 may identify whether the camera 720 is completely covered with the finger 402. In an embodiment, the processor 120 may identify whether the camera 720 is completely covered based on light acquired through an image sensor (not shown) of the camera 720. In an embodiment, if the light acquired through the image sensor (not shown) of the camera 720 includes light other than the reflection light of the light emitted from the display 710, the processor 120 may identify that the camera 720 is not completely covered with the finger 402. In an embodiment, if the light acquired through the image sensor (not shown) of the camera 720 does not include light other than the reflection light of the light emitted from the display 710, the processor 120 may identify that the camera 720 is completely covered with the finger 402.

In an embodiment, if the camera 720 is completely covered with the finger 402, the processor 120 may display the second user interface 713 for biometric measurement as shown in FIG. 7C. In an embodiment, if the camera 720 is not completely covered with the finger 402, the processor 120 may display a third user interface 715 including an indicator 714 which guides the user to retouch the display 710 with his or her finger 402 as shown in FIG. 7D.

In an embodiment, referring to FIG. 7C, the processor 120 may display the second user interface 713 on the display 710. In an embodiment, the processor 120 may set part of the second user interface 713 as an emissive area 750. In an embodiment, the processor 120 may set the emissive area 750 based on the touch area 740 of the finger 402. In an embodiment, the processor 120 may set the emissive area 750 so that its boundary is within the touch area 740 of the finger 402.

In an embodiment, the processor 120 may emit preset lights (e.g., the lights 461 and 463 of FIG. 4) from the emissive area 750 on the display 710. In an embodiment, the processor 120 may determine the color, intensity, or their combination of the lights 461 and 463, based on the type of the biometric information to be acquired.

In an embodiment, the processor 120 may emit the lights 461 and 463 from the emissive area 750 on the display 710, and measure the user's biometric information, based on the reflection lights 471 and 473 of the lights 461 and 463 acquired through the camera 720.

While the emissive area 750 of FIG. 7C shown in this example is in a ring shape, the instant disclosure is not so limited and the emissive area 750 may adopt various shapes. In an embodiment, referring to FIG. 8A, the electronic device 801 may include two or more emissive areas 851 and 852 on a display 810, where the display 810 is exposed through most of a front plate 830 of the electronic device 801. In an embodiment, the emissive areas 851 and 852 collectively may have a circular shape. In an embodiment, the emissive areas 851 and 852 may be disposed symmetrically around the center of the camera 820, by way of example. Alternatively, the emissive areas 851 and 852 may be disposed asymmetrically around the center of the camera 820.

In an embodiment, the processor 120 may control to illuminate the emissive areas 851 and 852 at different times. In an embodiment, the processor 120 may control to illuminate the emissive areas 851 and 852 in different colors.

In an embodiment, the processor 120 may control the emissive areas 851 and 852 to emit light of a first color (e.g., red) in a first time duration, and to emit light of a second color (e.g., green) in a second time duration. In an embodiment, the processor 120 may control to illuminate the emissive areas 851 and 852 in light of a color (e.g., yellow) mixed from the first color (e.g., red) and the second color (e.g., green).

Figures 8A, 8B, 8C:
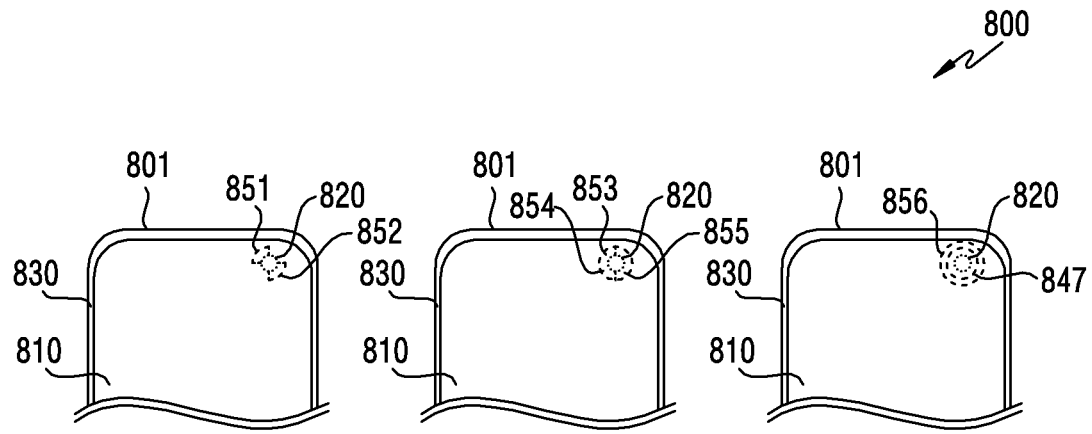
FIG. 8A is a view illustrating an example of an emissive area of an electronic device according to an embodiment.
FIG. 8B is a view illustrating an example of the emissive area of the electronic device according to an embodiment.
FIG. 8C is a view illustrating an example of the emissive area of the electronic device according to an embodiment.

In an embodiment, referring to FIG. 8B, an emissive area 853 of the display 810 exposed through most of the front plate 830 of the electronic device 801 may include two or more emissive subareas 854 and 855. In an embodiment, to emit the light in a preset pattern, the processor 120 may divide the emissive area 853 into two or more emissive subareas 854 and 855. In an embodiment, the processor 120 may control the display 810 to emit the light corresponding to the preset pattern from the emissive subareas 854 and 855.

In an embodiment, the processor 120 may control to illuminate the emissive subareas 854 and 855 at different times. In an embodiment, the processor 120 may control to illuminate the emissive subareas 854 and 855 in different colors.

In an embodiment, referring to FIG. 8C, emissive areas 856 and 857 of the display 810 exposed through most of the front plate 830 of the electronic device 801 may include the emissive area 857 directly adjacent to the camera 820 and the emissive area 856 in which the emissive area 857 is interposed between the emissive area 856 and the camera 820. In an embodiment, the processor 120 may control to illuminate the emissive areas 856 and 857 at different times. In an embodiment, the processor 120 may control to illuminate the emissive areas 856 and 857 in different colors. In an embodiment, the processor 120 may control to illuminate the emissive areas 856 and 857 so that light sources closer to the camera 820 emit light of relatively shorter wavelengths. For example, the emissive area 856, which is farther from the camera 820, may emit light of the first color (e.g., red), and the emissive area 857, which is closer to the camera 820, may emit light of the second color (e.g., green).

In an embodiment, the processor 120 may control to illuminate the emissive areas 856 and 857 with different intensities. In an embodiment, the processor 120 may control to illuminate the emissive area 856 with light of a first intensity, and to illuminate the emissive area 857 with light of a second intensity. In different embodiments, the first intensity may be higher or lower than the second intensity.

Figures 8D, 8E, 8F:
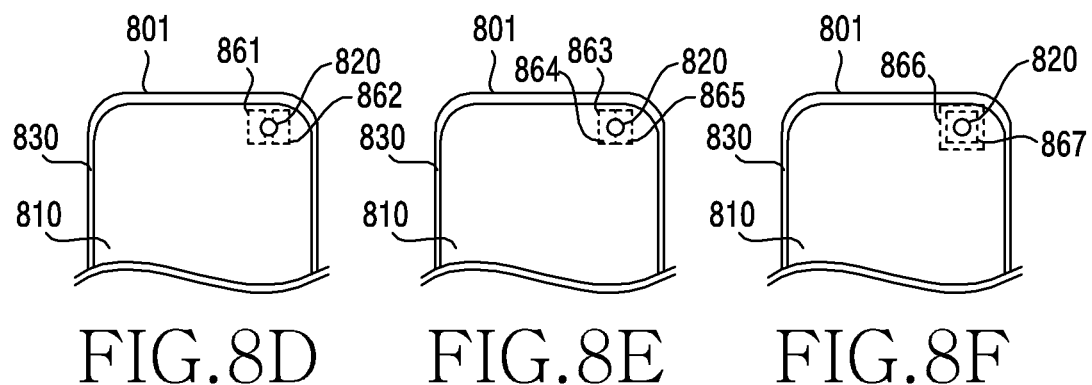
FIG. 8D is a view illustrating an example of the emissive area of the electronic device according to an embodiment.
FIG. 8E is a view illustrating an example of the emissive area of the electronic device according to an embodiment.
FIG. 8F is a view illustrating an example of the emissive area of the electronic device according to an embodiment.
Figure 8G:
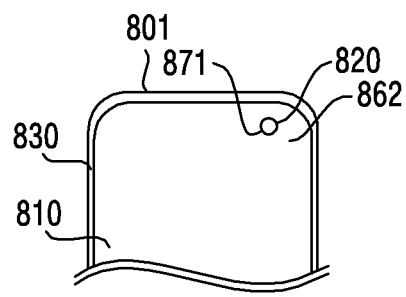
FIG. 8G is a view illustrating an example of the emissive area of the electronic device according to an embodiment.

In an embodiment, referring to FIG. 8D, two or more emissive areas 861 and 862 of the display 810 exposed through most of the front plate 830 of the electronic device 801 may be configured. In an embodiment, the emissive areas 861 and 862 together may form a quadrangular shape.

In an embodiment, referring to FIG. 8E, a quadrangular emissive area 863 of the display 810 exposed through most of the front plate 830 of the electronic device 801 may include two or more emissive subareas 864 and 865.

In an embodiment, referring to FIG. 8F, emissive areas 866 and 867 of the display 810 exposed through most of the front plate 830 of the electronic device 801 may include the quadrangular emissive area 867 directly adjacent to the camera 820 and the quadrangular emissive area 866, in which the emissive area 867 is interposed between the quadrangular emissive area 866 and the camera 820.

In an embodiment, referring to FIG. 8Q an emissive area 871 of the display 810 may be configured with an area of the same size as the camera 820. Accordingly, in this embodiment, the camera 820 is not disposed in a recess or opening of the display 810 but rather it overlaps with pixels of the display 810. In an embodiment, the emissive area 871 of the display 810 may emit light on a periodic basis. In an embodiment, in response to the periodic emission of the emissive area 871 of the display 810, the camera 280 may receive the reflected light of the light emitted from the emissive area 871 of the display 810. In an embodiment, light emission by the emissive area 871 and light detection by the camera 820 may be separated in time. In such an embodiment, the processor 120 may control the emissive area 871 not to emit light while the camera 820 is receiving light. In an embodiment, the processor 120 may set a shadow area (not shown) around the emissive area 871. In an embodiment, the shadow area (not shown) may emit light during the biometric measurement. In an embodiment, the shadow area (not shown) may be set within the touch area 740 of the finger 402.

The emissive areas 851, 852, 853, 856, 857, 861, 862, 863, 866, 867, and 871 are shown here either as circular or quadrangular. However, these are only examples, and the emissive areas may be additional shapes such as polygons.

In an embodiment, referring to FIG. 7D, if the processor 120 identifies that the camera 720 is not completely covered with the finger 402, the processor 120 may display the indicator 714 on the third user interface 715 which guides the user to retouch the display 510 with his or her finger 402. In an embodiment, the indicator 714 may be an image object in a shape indicating the camera 720 by way of example. The indicator 714 may include a phrase, an image, or their combination, for requesting the retouch.

In an embodiment, referring to FIG. 7E, if the indicator 714 is displayed and then the touch covering the camera 720 is identified, the processor 120 may identify whether the camera 720 is completely covered with the finger 402. In an embodiment, if it is identified that the camera 720 is completely covered by the retouch of the finger 402, the processor 120 may store position information of the indicator 714 in a memory (e.g., the memory 130 of FIG. 1).

In an embodiment, if the camera 720 is completely covered by the retouch of the finger 402, the processor 120 may display the second user interface 713 for the biometric measurement as shown in FIG. 7C. In an embodiment, if the camera 720 is not completely covered by the retouch of the finger 402, the processor 120 may display again the third user interface 715 including the indicator 714 that guides the user to retouch the display 710 as shown in FIG. 7D.

In an embodiment, the processor 120 may emit the lights 461 and 463 from the emissive area of the display 510 after the retouch of the finger 402 while displaying the second user interface 713, and measure the user's biometric information, based on the reflection lights 471 and 473 of the lights 461 and 463 acquired through the camera 520.

In an embodiment, while displaying the third user interface 715, the processor 120 may redisplay the indicator 714 which requests the retouch of the finger 402. In an embodiment, the processor 120 may display the indicator 714 at a redetermined position based on the touch area 741 of the finger 402.

FIGS. 9A through 9E are views each illustrating biometric information measurement using an electronic device 901 according to an embodiment. FIGS. 10A, 10B, and 10C are views each illustrating an example of an emissive area of an electronic device 1001 according to an embodiment. In an embodiment, the electronic device 901 of FIG. 9 or the electronic device 1001 of FIG. 10 may correspond to the electronic device 101 of FIG. 1 or the electronic device 401 of FIG. 4. In an embodiment, FIGS. 9A through 9E and FIGS. 10A, 10B, and 10C are described by referring to the configuration of the electronic device 101 of FIG. 1.

In an embodiment, referring to FIGS. 9A through 9E, a camera 920 of the electronic device 901 may not overlap a display 910, if the electronic device 701 is viewed in a first direction (e.g., a front direction of the electronic device 901). In an embodiment, the camera 920 may be disposed in an area where the display 910 is not exposed, on a front plate 930.

In an embodiment, referring to FIG. 9A, a processor (e.g., the processor 120) may display a first user interface 911 on the display 910.

In an embodiment, referring to FIG. 9B, the processor 120 may identify a touch covering the camera 920 with a user's finger (e.g., the finger 402 of FIG. 4), while the first user interface 911 is displayed on the display 910. In an embodiment, if the touch covering the camera 920 is identified, the processor 120 may display a second user interface 913 which is different from the first user interface 911 on the display 910.

In an embodiment, the processor 120 may identify the touch covering the camera 920, based on a touch area detected by a touch sensor (not shown) of the display 910 that corresponds to a touch area 940 of the finger 402. In an embodiment, if detecting the touch of the finger 402, the processor 120 may identify the touch covering the camera 920 based on an image acquired through the camera 920. In an embodiment, in response to the touch input in a preset area (e.g., an area adjacent to the camera 920 on the display 910) of the display 910, the processor 120 may enable the camera 920 and identify the touch covering the camera 920 based on the image acquired through the camera 920.

In an embodiment, if the touch covering the camera 920 is identified, the processor 120 may identify whether the camera 920 is completely covered with the finger 402. In an embodiment, the processor 120 may identify whether the camera 920 is completely covered based on light acquired through an image sensor (not shown) of the camera 920. In an embodiment, if the light acquired through the image sensor (not shown) of the camera 920 includes light other than the reflection light of the light emitted from the display 910, the processor 120 may identify that the camera 920 is not completely covered with the finger 402. In an embodiment, if the light acquired through the image sensor (not shown) of the camera 920 does not include light other than the reflection light of the light emitted from the display 910, the processor 120 may identify that the camera 920 is completely covered with the finger 402.

In an embodiment, if the camera 920 is completely covered with the finger 402, the processor 120 may display the second user interface 913 for biometric measurement as shown in FIG. 9C. In an embodiment, if the camera 920 is not completely covered with the finger 402, the processor 120 may display a third user interface 915 including an indicator 914 which guides the user to retouch the display 910 with his or her finger 402 as shown in FIG. 9D.

In an embodiment, referring to FIG. 9C, the processor 120 may display the second user interface 913 on the display

910. In an embodiment, the processor 120 may set part of the second user interface 913 as an emissive area 950. In an embodiment, the processor 120 may set the emissive area 950 based on the touch area 940 of the finger 402. In an embodiment, the processor 120 may set the emissive area 950 so that its boundary is within the touch area 940 of the finger 402. In an embodiment, the processor 120 may set the emissive area 950 close to the camera 920. In an embodiment, the processor 120 may determine the shape, pattern, size, position, or their combination of the emissive area 950, based on the type of the biometric information to be acquired, where the type may be selected by the user while the first user interface 911 is displayed.

In an embodiment, the processor 120 may emit preset lights (e.g., the lights 461 and 463 of FIG. 4) from the emissive area 950 on the display 910. In an embodiment, the processor 120 may determine the color, intensity, or their combination of the lights 461 and 463, based on the type of the biometric information to be acquired.

In an embodiment, the processor 120 may emit the lights 461 and 463 from the emissive area 950 on the display 910, and measure the user's biometric information, based on the reflection lights 471 and 473 of the lights 461 and 463 acquired through the camera 920.

While the emissive area 950 of FIG. 9C is shown in this example in an oval shape, the instant disclosure is not so limited and the emissive area 950 may adopt various shapes. In an embodiment, referring to FIG. 10A, an emissive area 1051 of a display 1010 may be quadrangular in shape, by way of example. The emissive area 1051 may have shapes such as polygons, circles, ovals, etc.

Referring to FIG. 10B, emissive areas 1053 and 1053 of the display 1010 may include two or more emissive areas. In an embodiment, the processor 120 may control to illuminate the emissive areas 1052 and 1053 at different times. Thus, in this embodiment, the processor 120 may control to illuminate the emissive area 1052 in a first time duration and to illuminate the emissive area 1053 in a second time duration.

In an embodiment, the processor 120 may control to illuminate the emissive areas 1052 and 1053 in different colors. In an embodiment, the processor 120 may emit light of a first color (e.g., red) from the emissive area 1052, and emit light of a second color (e.g., green) from the emissive area 1053 by way of example. Alternatively, the processor 120 may control to illuminate the emissive areas 1052 and 1053 in the same color.

In an embodiment, the processor 120 may control the emissive areas 1052 and 1053 to emit light of a first color (e.g., red) in a first time duration, and to emit light of a second color (e.g., green) in a second time duration. In an embodiment, the processor 120 may control to illuminate the emissive areas 1052 and 1053 in a color (e.g., yellow) mixed from the first color (e.g., red) and the second color (e.g., green).

In an embodiment, referring to FIG. 10C, an emissive area 1054 of the display 1010 may include two or more emissive subareas 1055 through 1058. In an embodiment, to emit the light in a preset pattern, the processor 120 may divide the emissive area 1054 into two or more emissive subareas 1055 through 1058. In an embodiment, the processor 120 may control the display 1010 to emit the light corresponding to the preset pattern from the emissive subareas 1055 through 1058.

In an embodiment, the processor 120 may control the emissive subareas 1055 through 1058 at different times. In an embodiment, the processor 120 may control to illuminate the emissive subareas 1055 through 1058 in different colors.

In an embodiment, referring to FIG. 9D, if the processor 120 identifies that the camera 920 is not completely covered with the finger 402, the processor 120 may display the indicator 914 on the third user interface 915 which guides the user to retouch the display 910 with his or her finger 402. In an embodiment, the indicator 914 may be an image object in a shape indicating the camera 920 by way of example. The indicator 914 may include a phrase, an image, or their combination, for requesting the retouch.

In an embodiment, the processor 120 may determine the position of the indicator 914, based on the position of the light other than the reflection light acquired through the image sensor (not shown) of the camera 920. The position of the light other than the reflection light may be a position corresponding to an area exposed to the light other than the reflection light. In an embodiment, if the position of the light other than the reflection light is in a first direction from the center of the camera 920, for example, the processor 120 may determine the position of the indicator 914 to be a position that is a set distance in the first direction away from a preset reference position. In an embodiment, the processor 120 may determine the set distance in response to the area exposed to the light other than the reflection light on the image acquired through the image sensor (not shown) of the camera 920. In an embodiment, the processor 120 may determine the set distance in response to the width of the area exposed to the light other than the reflection light.

In an embodiment, referring to FIG. 9E, if the indicator 914 is displayed and then the touch covering the camera 920 is identified, the processor 120 may identify whether the camera 920 is completely covered with the finger 402. In an embodiment, if it is identified that the camera 920 is completely covered by the retouch of the finger 402, the processor 120 may store position information of the indicator 914 in memory (e.g., the memory 130 of FIG. 1).

In an embodiment, if the camera 920 is completely covered by the retouch of the finger 402, the processor 120 may display the second user interface 913 for the biometric measurement as shown in FIG. 9C. In an embodiment, if the camera 920 is not completely covered by the retouch of the finger 402, the processor 120 may display again the third user interface 915 including the indicator 914 that guides the user to retouch the display 910 as shown in FIG. 9D.

In an embodiment, the processor 120 may emit the lights 461 and 463 from the emissive area of the display 910 after the retouch of the finger 402 while displaying the second user interface 913, and measure the user's biometric information, based on the reflection lights 471 and 473 of the lights 461 and 463 acquired through the camera 920.

In an embodiment, while displaying the third user interface 915, the processor 120 may redisplay the indicator 914 which requests the retouch of the finger 402. In an embodiment, the processor 120 may display the indicator 914 at a redetermined position based on the touch area 941 of the finger 402.

Figure 11:
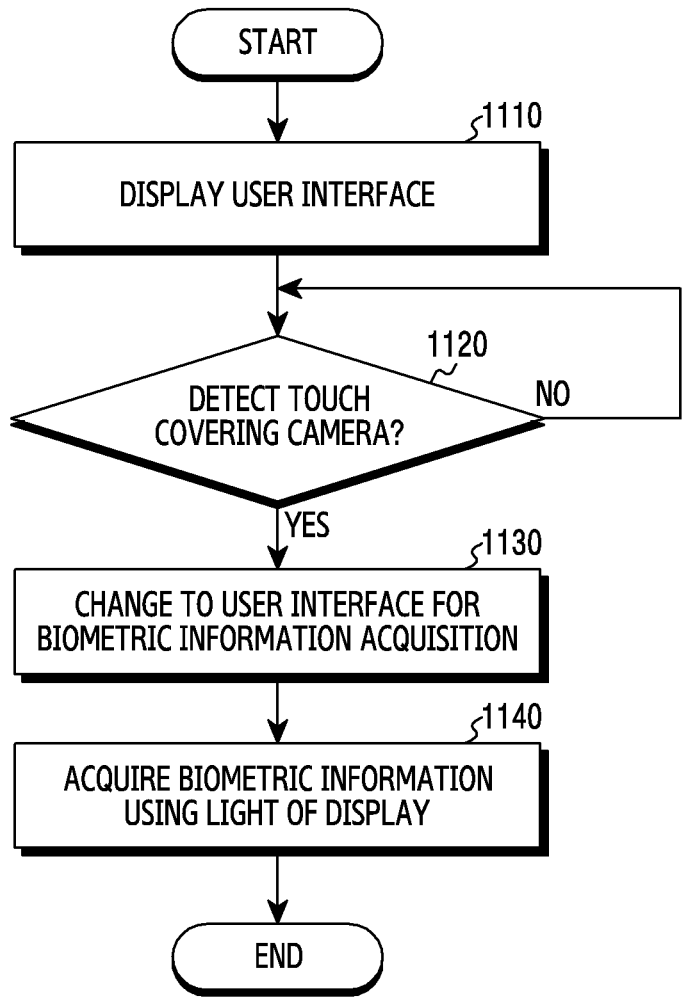
FIG. 11 illustrates a flowchart of operations of an electronic device according to an embodiment.

FIG. 11 illustrates a flowchart of operations of an electronic device (e.g., the electronic device 401 of FIG. 4) according to an embodiment. The operations of FIG. 11 shall be described by referring to the configurations of the electronic device 101 of FIG. 1 and the electronic device 401 of FIG. 4.

Referring to FIG. 11, in operation 1110, a processor (e.g., the processor 120 of FIG. 1) may display a user interface on a display (e.g., the display 410). In an embodiment, the user interface displayed in operation 1110, in connection with a sensor (e.g. touch sensor), may receive an input (e.g., a touch input) for selecting a type of user's biometric information to be measured while, for example, a biometric information measurement application is running. In an embodiment, the user interface may be generated by another running application that is different from the biometric information measurement application.

In an embodiment, the processor 120 may determine the type of the biometric information to acquire through the user interface displayed in operation 1110. In an embodiment, the biometric information may include, for example, heart rate, oxygen saturation, stress index, blood pressure, blood sugar, tissue hydration, tissue dehydration, fingerprint, or a combination thereof. The biometric information acquired with the reflection light is not limited thereto.

In operation 1120, the processor 120 may identify a touch which covers a camera (e.g., the camera 420) with the user's finger (e.g., the finger 402 of FIG. 4). In an embodiment, the processor 120 may identify the touch covering the camera 420, based on a touch area detected by a touch sensor (not shown) of the display 410 that corresponds to the touch area 440 of the finger 402. In an embodiment, if the detected touch area surrounds the camera 420, the processor 120 may identify the touch covering the camera 420. In an embodiment, if the touch of the finger 402 is detected, the processor 120 may identify the touch covering the camera 420 based on an image acquired through the camera 420. In an embodiment, in response to the touch input in a preset area (e.g., a preset area to surround the camera 420) of the display 410, the processor 120 may enable the camera 420 and identify the touch covering the camera 420 based on the image acquired through the camera 420.

In an embodiment, if the touch covering the camera 420 is identified ('YES'), the processor 120 may perform operation 1130. In an embodiment, if the touch covering the camera 420 is not identified ('NO'), the processor 120 may return to operation 1120.

In operation 1130, the processor 120 may change the user interface to a user interface for biometric information acquisition. In an embodiment, the user interface displayed in operation 1130 may be associated with the measurement of the user's biometric information while the biometric information measurement application is running.

In operation 1140, the processor 120 may acquire biometric information using light emitted from the display 410. In an embodiment, the processor 120 may acquire the biometric information, by emitting light (e.g., the lights 461 and 463 of FIG. 4) from an emissive area (e.g., the emissive area 450 of FIG. 4) of the user interface, obtaining reflection light (e.g., the lights 471 and 473 of FIG. 4) of the lights 461 and 463 through the camera 420, and analyzing the obtained reflection lights 471 and 473.

In an embodiment, the processor 120 may set part of the user interface as the emissive area 450. In an embodiment, the processor 120 may set the emissive area 450 based on the touch area 440 of the finger 402. In an embodiment, the processor 120 may set the emissive area 450 so that its boundary is within the touch area 440 of the finger 402. In an embodiment, the processor 120 may set the emissive area 450 to surround the camera 420. In an embodiment, the processor 120 may determine the shape, pattern, size, position, or their combination of the emissive area 450, based on the type of the biometric information to be acquired while the user interface is displayed in operation 1110.

In an embodiment, the processor 120 may emit preset light (e.g., the lights 461 and 463 of FIG. 4) from the emissive area 450 on the display 410. In an embodiment, the processor 120 may determine the color, intensity, or their combination of the lights 461 and 463, based on the type of the biometric information to be acquired while the user interface is displayed in operation 1110.

Figure 12:
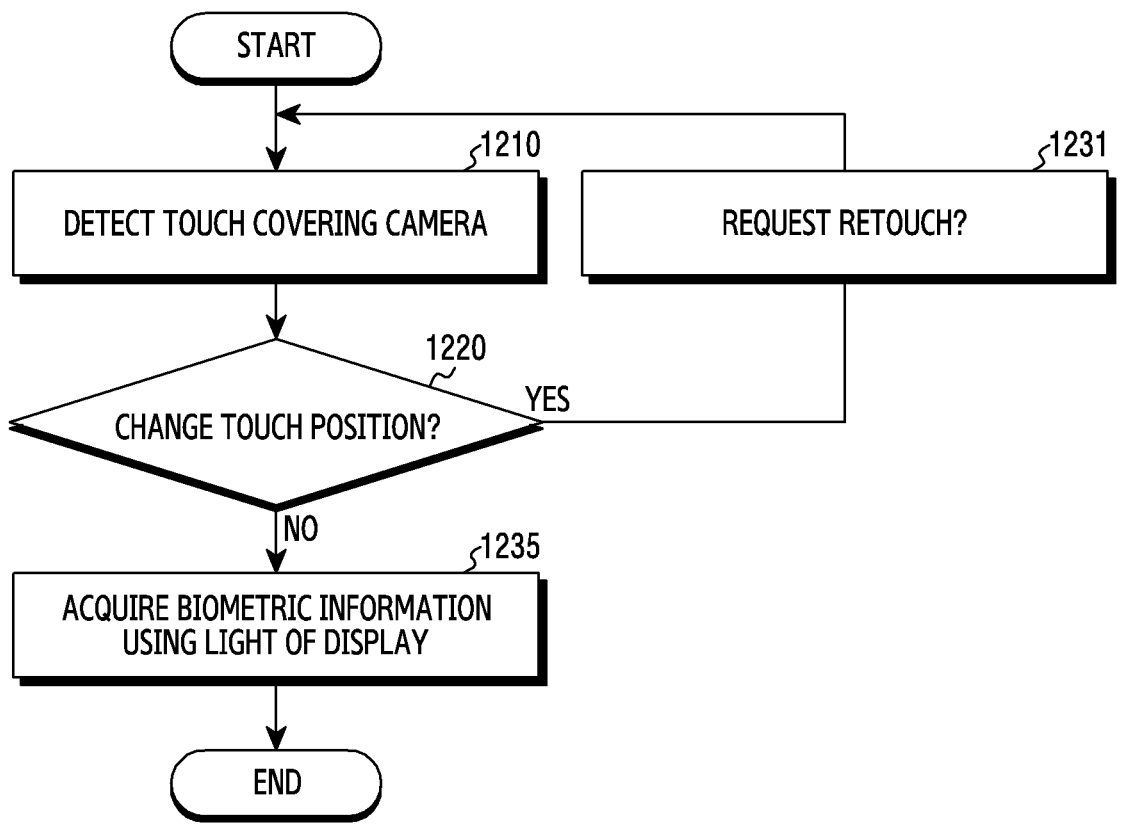
FIG. 12 illustrates a flowchart of operations of an electronic device according to an embodiment.

FIG. 12 illustrates a flowchart of operations of an electronic device (e.g., the electronic device 401 of FIG. 4) according to an embodiment. The operations of FIG. 12 shall be described by referring to the configurations of the electronic device 101 of FIG. 1 and the electronic device 401 of FIG. 4.

In an embodiment, operation 1210 of FIG. 12 may correspond to operation 1120 of FIG. 11. In an embodiment, operation 1235 of FIG. 12 may correspond to operation 1140 of FIG. 11.

Referring to FIG. 12, in operation 1210, a processor (e.g., the processor 120 of FIG. 1 may identify a touch which covers a camera (e.g., the camera 420) with a user's finger (e.g., the finger 402 of FIG. 4).

In operation 1220, the processor 120 may identify whether a change of the touch position is required. In an embodiment, if the camera 420 is not completely covered with the finger 402, the processor 120 may identify that it is necessary to change the touch position.

In an embodiment, if light acquired through an image sensor (not shown) of the camera 420 includes light other than the reflection light of light emitted from the display (e.g., the display 410 of FIG. 4), the processor 120 may identify that the camera 420 is not completely covered with the finger 402.

In an embodiment, if the processor 120 identifies that it is necessary to change the touch position ('YES'), the processor 120 may perform operation 1231. In an embodiment, if the processor 120 identifies that the touch position does not need to change ('NO'), the processor 120 may perform operation 1235.

In operation 1231, the processor 120 may guide the user to retouch the display 410. In an embodiment, the processor 120 may display an indicator requesting the retouch of the finger 402 on a user interface. In an embodiment, the position of the indicator requesting the retouch may be determined based on information stored in memory (e.g., the memory 130 of FIG. 1).

In an embodiment, the processor 120 may display the indicator requesting the retouch on the user interface, return to operation 1210, and thus re-detect the user touch. In an embodiment, if the user touch is released and then detected again, if the touch area 440 is changed, or a combination thereof occurs, the processor 120 may identify the user touch is re-detected. In an embodiment, if the processor 120 identifies that no additional retouches are required once the re-detected user touch is detected in operation 1220, the processor 120 may store position information of the indicator displayed in operation 1231 in memory (e.g., the memory 130 of FIG. 1).

In operation 1235, the processor 120 may acquire biometric information using light emitted from the display 410. In an embodiment, the processor 120 may acquire the biometric information, by emitting light (e.g., the lights 461 and 463 of FIG. 4) from an emissive area (e.g., the emissive area 450 of FIG. 4) of the user interface, obtaining reflection light (e.g., the lights 471 and 473 of FIG. 4) of the lights 461 and 463 through the camera 420, and analyzing the obtained reflection lights 471 and 473.

As set forth above, the electronic device (e.g., the electronic device 401 of FIG. 4) and its operating method may provide the user with various functions associated with biometric information acquisition, without dedicated light emitting devices and optical sensors.

As mentioned above, an electronic device (e.g., the electronic device 401 of FIG. 4) may include a housing, a display exposed through at least part of a first surface of the housing, an image sensor exposed through at least part of the first surface of the housing, a processor operatively connected with the display and the image sensor, and a memory operatively connected with the processor. The memory may store instructions that, when executed, cause the processor to detect a touch of a finger of a user on the image sensor, while displaying a user interface using the display, in response to detecting the touch, while the touch of the finger is maintained on the image sensor, change the user interface in an area of the display within a preset distance from the image sensor, and acquire biometric information of the user based on reflection light of light emitted from the display, where the reflection light is acquired using the image sensor.

In an embodiment, the instructions may cause the processor to emit light with a first intensity in the area of the display within the preset distance from the image sensor before detecting the touch, and in response to detecting the touch, emit light with a second intensity higher than the first intensity in the area of the display within the preset distance from the image sensor.

In an embodiment, the instructions may cause the processor to, in response to receiving, at the image sensor, light other than the reflection light, display another user interface to guide the user to retouch the display.

In an embodiment, the instructions may cause the processor to, in response to detecting the touch, identify an area where the finger of the user touches on the display, and based on the identified area, set the area of the display within the preset distance from the image sensor.

In an embodiment, the image sensor may be disposed in a display area of the display, when viewed in a front view of the housing.

In an embodiment, the area of the display within the preset distance from the image sensor may surround the image sensor, when viewed in a front view of the housing.

In an embodiment, the instructions may cause the processor to, in response to detecting the touch, while the touch of the finger is maintained on the image sensor, change the user interface at designated time intervals.

In an embodiment, the instructions may cause the processor to, in response to detecting the touch, emit light of a first intensity from a first portion of the area of the display within the preset distance from the image sensor, and in response to detecting the touch, emit light of a second intensity higher than the first intensity from a second portion of the area of the display within the preset distance from the image sensor.

In an embodiment, the instructions may cause the processor to receive an input, based on the received input, identify first biometric information to be acquired from the user, and in response to detecting the touch, emit light corresponding to the identified first biometric information from the area of the display within the preset distance from the image sensor.

As mentioned above, an operating method of an electronic device (e.g., the electronic device 401 of FIG. 4) may include, while displaying a user interface using a display exposed through at least part of a first surface of a housing, detecting a touch of a finger of a user on an image sensor exposed through at least part of the first surface of the housing, in response to detecting the touch, while the touch of the finger is maintained on the image sensor, changing the user interface in an area of the display within a preset distance from the image sensor, and acquiring biometric information of the user based on reflection light of light emitted from the display, where the reflection light is acquired using the image sensor.

In an embodiment, light with a first intensity is emitted in the area of the display within the preset distance from the image sensor before detecting the touch, and in response to detecting the touch, light with a second intensity higher than the first intensity is emitted in the area of the display within the preset distance from the image sensor.

In an embodiment, the method may further include, in response to receiving, at the image sensor, light other than the reflection light, displaying another user interface to guide the user to retouch the display.

In an embodiment, the method may further include, in response to detecting the touch, identifying an area where the finger of the user touches on the display, and based on the identified area, setting the area of the display within the preset distance from the image sensor.

In an embodiment, the image sensor may be disposed in a display area of the display, when viewed in a front view of the housing, and the area of the display within the preset distance from the image sensor may surround the image sensor, when viewed in the front view of the housing.

In an embodiment, the method may further include, in response to detecting the touch, emitting light of a first intensity from a first portion of the area of the display within the preset distance from the image sensor, and in response to detecting the touch, emitting light of a second intensity higher than the first intensity from a second portion of the area of the display within the preset distance from the image sensor.

In an embodiment, the method may further include receiving an input, based on the received input, identifying first biometric information to be acquired from the user, and in response to detecting the touch, emitting light corresponding to the identified first biometric information from the area of the display within the preset distance from the image sensor.

In an embodiment, the method may further include identifying asymmetry with respect to a reference direction of an image acquired by the image sensor based on the reflection light, in response to identifying the asymmetry with respect to the reference direction of the image, identifying a degree of the asymmetry with respect to the reference direction of the image, and based on the identified degree of the asymmetry, changing the area of the display within the preset distance.

As mentioned above, an electronic device (e.g., the electronic device 401 of FIG. 4) may include a housing, a display exposed through at least part of a first surface of the housing, an image sensor disposed in a display area of the display, when viewing the first surface of the housing, a processor operatively connected with the display and the image sensor, and a memory operatively connected with the processor, wherein the memory may store instructions that, when executed, cause the processor to display an indicator indicating a preset touch request area, on a user interface displayed on the display, detect a touch of a finger of a user, in at least part of the touch request area after the indicator is displayed in the user interface, in response to detecting the touch, control the display to emit light of a preset intensity in a preset second area which surrounds the image sensor, when viewed in a front view of the housing, and acquire biometric information of the user based on reflection light of the light of the preset intensity emitted from the display, where the reflection light is acquired using the image sensor.

In an embodiment, characteristics of light emitted from a first portion of the second area are different from characteristics of light emitted from a second portion of the second area.

In an embodiment, the instructions may cause the processor to, in response to receiving, at the image sensor, light other than the reflection light, display another user interface to guide the user to retouch the display.

In an embodiment, the instructions may cause the processor to adjust a position of the indicator, based on an image acquired by the image sensor based on the reflection light, display the indicator at the adjusted position, on the user interface displayed on the display, after displaying the indicator at the adjusted position, detect a retouch of the finger of the user, and in response to detecting the retouch of the finger of the user, when biometric information of the user based on the reflection light is acquired, store the adjusted position of the indicator on the user interface, in the memory.

Methods according to an embodiment of the present disclosure may be implemented in hardware, software, or a combination of hardware and software.

When the methods are implemented by software, a computer-readable storage medium for storing one or more programs (software modules) may be provided. The one or more programs stored in the computer-readable storage medium may be configured for execution by one or more processors within the electronic device. The one or more program may include instructions that cause the electronic device to perform the methods according to an embodiment of the present disclosure as defined by the appended claims and/or disclosed herein.

The programs (software modules or software) may be stored in non-volatile memories including a random access memory and a flash memory, a read only memory (ROM), an electrically erasable programmable read only memory (EEPROM), a magnetic disc storage device, a compact disc-ROM (CD-ROM), digital versatile discs (DVDs), or other type optical storage devices, or a magnetic cassette. Any combination of some or all of them may form a memory in which the program is stored. Further, a plurality of such memories may be included in the electronic device.

In addition, the programs may be stored in an attachable storage device which is accessible through communication networks such as the Internet, Intranet, local area network (LAN), wide area network (WAN), and storage area network (SAN), or a combination thereof. Such a storage device may access the electronic device via an external port. Further, a separate storage device on the communication network may access a portable electronic device.

In the above-described example embodiments of the present disclosure, a component included in the present disclosure is expressed in the singular or the plural according to a presented example embodiment. However, the singular form or plural form is selected for convenience of description suitable for the presented situation, and an embodiment of the present disclosure are not limited to a single element or multiple elements thereof. Further, either multiple elements expressed in the description may be configured into a single element or a single element in the description may be configured into multiple elements.

Certain of the above-described embodiments of the present disclosure can be implemented in hardware, firmware or via the execution of software or computer code that can be stored in a recording medium such as a CD ROM, a Digital Versatile Disc (DVD), a magnetic tape, a RAM, a floppy disk, a hard disk, or a magneto-optical disk or computer code downloaded over a network originally stored on a remote recording medium or a non-transitory machine readable medium and to be stored on a local recording medium, so that the methods described herein can be rendered via such software that is stored on the recording medium using a general purpose computer, or a special processor or in programmable or dedicated hardware, such as an ASIC or FPGA. As would be understood in the art, the computer, the processor, microprocessor controller or the programmable hardware include memory components, e.g., RAM, ROM, Flash, etc. that may store or receive software or computer code that when accessed and executed by the computer, processor or hardware implement the processing methods described herein.

While the present disclosure has been illustrated and described with reference to an example embodiment thereof, it will be understood by those skilled in the art that various changes in form and details may be made therein without departing from the true spirit and full scope of the present disclosure.

What is claimed is:

1. An electronic device comprising:
a housing;
a display exposed through at least part of a first surface of the housing, the display including an opening;
an image sensor exposed through the opening in the display and at least part of the first surface of the housing;
a processor operatively connected with the display and the image sensor; and
a memory operatively connected with the processor,
wherein the memory stores instructions that, when executed, cause the processor to:
detect a touch of a finger of a user on the image sensor, while displaying a user interface using the display,
in response to detecting the touch, while the touch of the finger is maintained on the image sensor, change the user interface in first area and a second area of the display, the first area adjacent to the opening in the display within a preset distance from the image sensor, and the second area proximate to the first area, and
acquire biometric information of the user based on reflected light of light emitted from the first area and from the second area of the display, wherein the reflected light is acquired using the image sensor,
wherein a size of the first area adjacent to the opening for emission of the light is set based in part on a size of a contact area of the detected touch, and
wherein the light is emitted from the first area and the second area according to at least one of: illumination at different times, and illumination using different colors.

2. The electronic device of claim 1, wherein the instructions further cause the processor to:
emit light with a first intensity in the first area of the display within the preset distance from the image sensor before detecting the touch, and
in response to detecting the touch, emit light with a second intensity higher than the first intensity in the first area of the display within the preset distance from the image sensor.

3. The electronic device of claim 1, wherein the instructions further cause the processor to:
in response to receiving, at the image sensor, light other than the reflected light, display another user interface to guide the user to retouch the display.

4. The electronic device of claim 1, wherein the instructions further cause the processor to:
in response to detecting the touch, identify third area where the finger of the user touches on the display, and
based on the identified third area, set the first area of the display within the preset distance from the image sensor.

5. The electronic device of claim 1, wherein the image sensor is disposed in a display area of the display, when viewed in a front view of the housing.

6. The electronic device of claim 1, wherein the instructions further cause the processor to:
in response to detecting the touch, while the touch of the finger is maintained on the image sensor, change the user interface at designated time intervals.

7. The electronic device of claim 1, wherein the instructions further cause the processor to:
in response to detecting the touch, emit light of a first intensity from the first area of the display within the preset distance from the image sensor, and
in response to detecting the touch, emit light of a second intensity higher than the first intensity from the second area of the display.

8. The electronic device of claim 1, wherein the instructions further cause the processor to:
receive an input,
based on the received input, identify first biometric information to be acquired from the user, and
in response to detecting the touch, emit light corresponding to the identified first biometric information from the first area of the display within the preset distance from the image sensor.

9. An operating method of an electronic device that includes a housing, the method comprising:
displaying a user interface using a display including an opening, the display exposed through at least part of a first surface of the housing,
detecting a touch of a finger of a user on an image sensor exposed through opening in the display and at least part of the first surface of the housing;
in response to detecting the touch, while the touch of the finger is maintained on the image sensor, changing the user interface in a first area and a second area of the display, the first area adjacent to the opening in the display within a preset distance from the image sensor, and the second area proximate to the first area; and
acquiring biometric information of the user based on reflected light of light emitted from the first area and from the second area of the display, wherein the reflected light is acquired using the image sensor,
wherein a size of the first area adjacent to the opening for emission of the light is set based in part on a size of a contact area of the detected touch, and
wherein the light is emitted from the first area and the second area according to at least one of: illumination at different times, and illumination using different colors.

10. The method of claim 9, wherein light with a first intensity is emitted in the first area of the display within the preset distance from the image sensor before detecting the touch, and
in response to detecting the touch, light with a second intensity higher than the first intensity is emitted in the first area of the display within the preset distance from the image sensor.

11. The method of claim 9, further comprising:
in response to receiving, at the image sensor, light other than the reflected light, displaying another user interface to guide the user to retouch the display.

12. The method of claim 9, further comprising:
in response to detecting the touch, identifying an area where the finger of the user touches on the display; and
based on the identified area, setting the first area of the display within the preset distance from the image sensor.

13. The method of claim 9, wherein the image sensor is disposed in a display area of the display, when viewed in a front view of the housing.

14. The method of claim 9, further comprising:
in response to detecting the touch, emitting light of a first intensity from the first area of the display within the preset distance from the image sensor; and
in response to detecting the touch, emitting light of a second intensity higher than the first intensity from the second area of the display.

15. The method of claim 9, further comprising:
receiving an input;
based on the received input, identifying first biometric information to be acquired from the user; and
in response to detecting the touch, emitting light corresponding to the identified first biometric information from the first area of the display within the preset distance from the image sensor.

16. The method of claim 9, further comprising:
identifying asymmetry with respect to a reference direction of an image acquired by the image sensor based on the reflected light;
in response to identifying the asymmetry with respect to the reference direction of the image, identifying a degree of the asymmetry with respect to the reference direction of the image; and
based on the identified degree of the asymmetry, changing the first area of the display within the preset distance.

17. An electronic device comprising:
a housing;
a display exposed through at least part of a first surface of the housing, the display including an opening;
an image sensor exposed through the opening in the display and disposed in a display area of the display, when viewing the first surface of the housing;
a processor operatively connected with the display and the image sensor; and
a memory operatively connected with the processor,
wherein the memory stores instructions that, when executed, cause the processor to:
display an indicator indicating a preset touch request area, on a user interface displayed on the display,
detect a touch of a finger of a user, in at least part of the touch request area after the indicator is displayed in the user interface,
in response to detecting the touch, control the display to emit light of a preset intensity in a preset second area adjacent to the opening in the display through which the image sensor is exposed when viewed in a front view of the housing, and in a preset third area proximate to the preset second area, and
acquire biometric information of the user based on reflected light of the light of the preset intensity emitted from preset second area and the preset third area of the display, wherein the reflected light is acquired using the image sensor, wherein a size of the preset second area adjacent to the opening for emission of the light is set based in part on a size of a contact area of the detected touch, and wherein the light is emitted from the preset second area and the preset third area according to at least one of: illumination at different times, and illumination using different colors.

18. The electronic device of claim 17, wherein characteristics of light emitted from the preset second area are different from characteristics of light emitted from the preset third area.

19. The electronic device of claim 17, wherein the instructions further cause the processor to:

in response to receiving, at the image sensor, light other than the reflected light, display another user interface to guide the user to retouch the display.

20. The electronic device of claim 17, wherein the instructions further cause the processor to:

adjust a position of the indicator, based on an image acquired by the image sensor based on the reflected light, display the indicator at the adjusted position, on the user interface displayed on the display, after displaying the indicator at the adjusted position, detect a retouch of the finger of the user, and in response to detecting the retouch of the finger of the user, when biometric information of the user based on the reflected light is acquired, store the adjusted position of the indicator on the user interface, in the memory.

* * * * *